(12) United States Patent
Horne et al.

(10) Patent No.: US 10,155,732 B2
(45) Date of Patent: *Dec. 18, 2018

(54) RIBONUCLEOTIDE REDUCTASE INHIBITORS AND METHODS OF USE

(71) Applicant: City of Hope, Duarte, CA (US)

(72) Inventors: David Horne, Altadena, CA (US); Christopher Lincoln, La Canada, CA (US)

(73) Assignee: City of Hope, Duarte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/725,181

(22) Filed: Oct. 4, 2017

(65) Prior Publication Data

US 2018/0155303 A1 Jun. 7, 2018

Related U.S. Application Data

(60) Continuation of application No. 15/418,366, filed on Jan. 27, 2017, now Pat. No. 9,796,692, which is a division of application No. 14/754,100, filed on Jun. 29, 2015, now Pat. No. 9,598,385, which is a continuation of application No. 14/444,172, filed on Jul. 28, 2014, now Pat. No. 9,126,960, which is a continuation of application No. PCT/US2013/024490, filed on Feb. 1, 2013, which is a continuation of application No. 13/364,263, filed on Feb. 1, 2012, now Pat. No. 8,372,983.

(51) Int. Cl.
| | | |
|---|---|---|
| *C07D 277/46* | (2006.01) |
| *C07C 45/68* | (2006.01) |
| *C07D 277/40* | (2006.01) |
| *C07D 417/12* | (2006.01) |

(52) U.S. Cl.
CPC ............ *C07D 277/46* (2013.01); *C07C 45/68* (2013.01); *C07D 277/40* (2013.01); *C07D 417/12* (2013.01)

(58) Field of Classification Search
CPC .. C07D 277/46; C07D 277/40; C07D 417/12; C07C 45/68
USPC ........................................................ 548/195
See application file for complete search history.

(56) References Cited

U.S. PATENT DOCUMENTS

| | | |
|---|---|---|
| 7,956,076 B2 | 6/2011 | Yen et al. |
| 8,372,983 B2 | 2/2013 | Horne et al. |
| RE45,020 E | 7/2014 | Horne et al. |
| 9,126,960 B2 | 9/2015 | Horne et al. |
| 9,598,385 B2 | 3/2017 | Horne et al. |
| 9,796,692 B2 | 10/2017 | Horne et al. |
| 2009/0258915 A1 | 10/2009 | Yen et al. |

FOREIGN PATENT DOCUMENTS

| | | |
|---|---|---|
| CN | 1794988 A | 6/2006 |
| CN | 101096363 A | 1/2008 |
| CN | 102070555 A | 5/2011 |
| EP | 0790057 A1 | 8/1997 |
| EP | 2 042 494 A1 | 4/2009 |
| WO | WO-2004/087138 A1 | 10/2004 |
| WO | WO-2013/116765 A1 | 8/2013 |

OTHER PUBLICATIONS

Angus, S. P., et al., "Retinoblastoma Tumor Suppressor Targets dNTP Metabolism to Regulate DNA Replication," J. Biol. Chem. 277:44376-44384 (2002).
Berge, S. M., et al., "Pharmaceutical Salts," J. Pharm. Sci. 66:1-19 (1977).
Brevitt, S.E. et al. (Jun. 20, 1997). "Synthesis and in vitro evaluation of two progressive series of bifunctional polyhydroxybenzamide catechol-O-methyltransferase inhibitors," *J Med Chem* 40(13):2035-2039.
Cancer [online], retrieved from the Internet on Jul. 6, 2007, URL:<http://www.nlm.nih.gov/medlineplus/cancer.html.>.
Cancer [online], retrieved from the Internet on Jul. 6, 2007, URL:<http://en.wikipedia.org/wiki/Cancer.>.
Chabes, A.L., et al., "S Phase-specific Transcription of the Mouse Ribonucleotide Reductase R2 Gene Requires Both a Proximal Repressive E2F-binding Site and an Upstream Promoter Activating Region," J. Biol. Chem. 279:10796-10807 (2004).
Chang, C. H., et al., "Substrate Specificity of Human Ribonucleotide Reductase from Molt-4F Cells," Cancer Res. 39:5081-5086 (1979).
Chen, S., et al., "Inhibition of Human Cancer Cell Growth by Inducible Expression of Human Ribonucleotide Reductase Antisense cDNA," Antisense Nucleic Acid Drug Dev. 10:111-116 (2000).
Cooperman, B. S., et al., "A Comprehensive Model for the Allosteric Regulation of Class Ia Ribonucleotide Reductases," Adv. Enzyme Regul. 43:167-182 (2003).
Cory, J. G., et al., "Regulation of Ribonucleotide Reductase Activity in Mammalian Cells," Mol. Cell. Biochem. 53-54:257-266 (1983).
Currie, R.A., et al., "NF-Y Is Associated with the Histone Acetyltransferases GCN5 and P/CAF," J. Biol. Chem. 273:1430-1434 (1998).
Elledge, S.J., et al., "Two Genes Differentially Regulated in the Cell Cycle and by DNA-Damaging Agents Encode Alternative Regulatory Subunits of Ribonucleotide Reductase," Genes Dev. 4:740-751 (1990).
Fan, H., et al., "The Mammalian Ribonucleotide Reductase R2 Component Cooperates with a Variety of Oncogenes in Mechanisms of Cellular Transformation," Cancer Res. 58:1650-1653 (1998).
Fan, H., et al., "The R1 Component of Mammalian Ribonucleotide Reductase Has Malignancy-Suppressing Activity as Demonstrated by Gene Transfer Experiments," Proc. Nat. Acad. Sci. USA 94:13181-13186 (1997).

(Continued)

*Primary Examiner* — Kristin A Vajda
(74) *Attorney, Agent, or Firm* — Mintz Levin Cohn Ferris Glovsky and Popeo, P.C.

(57) ABSTRACT

Provided herein are novel compounds that inhibit ribonucleotide reductase (RR) by binding to RRM2 and interfering with the activity of the RRM1/RRM2 holoenzyme, as well as methods of synthesizing these novel compounds. The compounds may be used to inhibit RR activity and to treat various conditions associated with RRM2 expression, such as for example certain cancer types, mitochondrial diseases, or degenerative diseases.

20 Claims, 22 Drawing Sheets

(56) References Cited

OTHER PUBLICATIONS

Filatov, D., et al., "Role of a Proximal NF-Y Binding Promoter Element in S Phase-Specific Expression of Mouse Ribonucleotide Reductase R2 Gene," J. Biol. Chem. 270:25239-25243 (1995).

Goan, Y.G., et al., "Overexpression of Ribonucleotide Reductase as a Mechanism of Resistance to 2,2-Difluorodeoxycytidine in the Human KB Cancer Cell Line," Cancer Res. 59:4204-4207 (1999).

Golub, T. R., et al., "Molecular Classification of Cancer: Class Discovery and Class Prediction by Gene Expression Monitoring," Science 286:531-537 (1999).

Guittet, 0., et al., "Mammalian p53R2 Protein Forms an Active Ribonucleotide Reductase in Vitro with the R1 Protein, Which Is Expressed Both in Resting Cells in Response to DNA Damage and in Proliferating Cells," J. Biol. Chem. 276:40647-40651 (2001).

Huang, A., et al., "Ribonucleotide Reductase R2 Gene Expression and Changes in Drug Sensitivity and Genome Stability," Cancer Res. 57:4876-4881 (1997).

Jordan, A., et al., "Ribonucleotide Reductases," Annu. Rev. Biochem. 67:71-98 (1998).

Kimura, T., et al., "Impaired Function of p53R2 in Rrm2b-null Mice Causes Severe Renal Failure Through Attenuation of dNTP Pools," Nat. Genet. 34:440-445 (2003).

Kuschak, T. I., et al., "The Ribonucleotide Reductase R2 Gene is a Non-Transcribed Target of c-Myc-Induced Genomic Instability," Gene 238:351-365 (1999).

Lala, P. K., et al., "Role of Nitric Oxide in Tumor Progression: Lessons from Experimental Tumors," Cancer and Metastasis Reviews 17:91-106 (1998).

Lassmann, G., et al., "EPR Stopped-Flow Studies of the Reaction of the Tyrosyl Radical of Protein R2 from Ribonucleotide Reductase with Hydroxyurea," Biochem. Biophys. Res. Commun. 188:879-887 (1992).

Le, N.T., et al., "The Role of Iron in Cell Cycle Progression and the Proliferation of Neoplastic Cells," Biochim. Biophys. Acta 1603:31-46 (2002).

Liu, X., et al, "Nuclear Factor Y Regulation and Promoter Transactivation of Human Ribonucleotide Reductase Subunit M2 Gene in a Gemcitabine Resistant KB Clone," Biochem. Pharmacol. 67:1499-1511 (2004).

Liu, X., et al., "Metastasis-Suppressing Potential of Ribonucleotide Reductase Small Subunit p53R2 in Human Cancer Cells," Clin. Cancer Res. 12:6337-6344 (2006).

Liu, X., et al., "The Ribonucleotide Reductase Subunit M2B Subcellular Localization and Functional Importance for DNA Replication in Physiological Growth of KB Cells," Biochem. Pharmacol. 70:1288-1297 (2005).

Lozano, G., et al., "p53 Sends Nucleotides to Repair DNA," Nature 404:24-25 (2000).

Nakano, K., et al., "A Ribonucleotide Reductase Gene is a Transcriptional Target of p53 and p73," Oncogene 19:4283-4289 (2000).

Nocentini, G., et al., "Ribonucleotide Reductase Inhibitors: New Strategies for Cancer Chemotherapy," Grit. Rev. Oncol. Hematol. 22:89-126 (1996).

Nyholm, S., et al., "Reduction and Loss of the Iron Center in the Reaction of the Small Subunit of Mouse Ribonucleotide Reductase with Hydroxyurea," Biochem. 32:11569-11574 (1993).

Ochiai, E. I., et al., "Tyrosyl Free Radical Formation in the Small Subunit of Mouse Ribonucleotide Reductase," J. Biol. Chem. 265:15758-15761 (1990).

Shao, J., et al., "Determination of the Potency and Subunit-Selectivity of Ribonucleotide Reductase Inhibitors with a Recombinant-Holoenzyme-Based in Vitro Assay," Biochem. Pharmacol. 69:627-634 (2005).

Tanaka, H., et al., "A Ribonucleotide Reductase Gene Involved in a p53-Dependent Cell-Cycle Checkpoint for DNA Damage," Nature 404:42-49 (2000).

Thelander, L., et al., "Isolation and Characterization of Expressible eDNA Clones Encoding the M1 and M2 Subunits of Mouse Ribonucleotide Reductase," Mol. Cell. Biol. 6:3433-3442 (1986).

Vippagunta et al., Crystalline solids, 2001, Advanced Drug Delivery Reviews, 48, pp. 3 and 18.

Wolff et al., Burger's Medicinal Chemistry and Drug Discovery, 1994, Wiley-Interscience, Fifth Edition, vol. 1: Principles and Practice, pp. 975-977.

Wright, J. A., et al., "Regulation and Drug Resistance Mechanisms of Mammalian Ribonucleotide Reductase, and the Significance of DNA Synthesis," Biochem. Cell. Biol. 68:1364-1371 (1990).

Wuts, P.G.M. et al. (Apr. 10, 2006). "Protection for Phenols and Catechols Protection for Phenols 370 Ethers 370 Methyl," Greene's Protective Groups in Organic Synthesis, Fourth Edition pp. 367-430.

Xue, L., et al., "Wild-Type p53 Regulates Human Ribonucleotide Reductase by Protein-Protein Interaction with p53R2 as well as hRRM2 Subunits," Cancer Res. 63:980-986 (2003).

Yamaguchi, T., et al., "p53R2-Dependent Pathway for DNA Synthesis in a p53-Regulated Cell Cycle Checkpoint," Cancer Res. 61:8256-8262 (2001).

Yen, Y., et al., "Characterization of a Hydroxyurea-Resistant Human KB Cell Line with Supersensitivity to 6-Thioguanine," Cancer Res. 54:3686-3691 (1994).

Zhan J. et al. (Dec. 31, 2004). "Synthesis of Dioxybenzoin," *Chemical World* 9: 481-483. (Translation of Abstract only).

Zhou, B.S., et al., "Overexpression of Ribonucleotide Redactase in Transfected Human KB Cells Increases Their Resistance to Hydroxyurea: M2 but not Ml Is Sufficient to Increase Resistance to Hydroxyurea in Transfected Cells," Cancer Res. 55:1328-1333 (1995).

Zhou, B.S., et al., "Overexpression of Transfected Human Ribonucleotide Reductase M2 Subunit in Human Cancer Cells Enhances Their Invasive Potential," Clin. Exp. Metastasis 16:43-49 (1998).

Zhou, B.S., et al., "The Human Ribonucleotide Reductase Subunit hRRM2 Complements p53R2 in Response to UV-Induced DNA Repair in Cells with Mutant p53," Cancer Res. 63:6583-6594 (2003).

FIG. 3C  Comparison of RR expression and migration ability of Vector, and RRM2 sense transfectants

| | Relative RRM2 protein amount [a] | Migration Cell number field (range) |
|---|---|---|
| KB cell | | |
| KBV | 1.0 | 12 (10-14) |
| KBM2 | 4.2 | 235.5 (185-286) |
| | | |
| PC3 cell | | |
| PC3V | 1.0 | 21.5 (18-25) |
| PC3M2 | 2.3 | 27.5 (25-30) | a. The protein expression level was determined by using Western Blot analysis. The relative amount of protein was normalized using a control vector transfectant.

* Represents solubility difficulties

Control

3-AP 3µM

COH20 9µM

COH20 27µM

FIG. 23

| Panel/Cell Line | Time Zero | Ctrl | Mean Optical Densities -8.0 | -7.0 | -6.0 | -5.0 | -4.0 | Percent Growth -8.0 | -7.0 | -6.0 | -5.0 | -4.0 | GI50 | TGI | LC50 |
|---|---|---|---|---|---|---|---|---|---|---|---|---|---|---|---|
| Leukemia | | | | | | | | | | | | | | | |
| CCRF-CEM | 0.250 | 1.543 | 1.485 | 1.399 | 1.181 | 0.369 | 0.270 | 94 | 69 | 72 | 9 | 2 | 2.24E-6 | > 1.00E-4 | > 1.00E-4 |
| HL-60(TB) | 0.283 | 0.859 | 0.921 | 1.010 | 0.733 | 0.326 | 0.200 | 111 | 126 | 78 | 7 | -29 | 2.50E-6 | 1.59E-5 | > 1.00E-4 |
| K-562 | 0.132 | 0.763 | 0.768 | 0.683 | 0.580 | 0.201 | 0.098 | 101 | 87 | 71 | 11 | -26 | 2.24E-6 | 1.97E-5 | > 1.00E-4 |
| MOLT-4 | 0.170 | 0.470 | 0.475 | 0.500 | 0.349 | 0.204 | 0.147 | 102 | 110 | 60 | 11 | -14 | 1.58E-6 | 2.86E-5 | > 1.00E-4 |
| RPMI-8226 | 0.224 | 0.907 | 0.878 | 0.827 | 0.787 | 0.499 | 0.206 | 96 | 88 | 82 | 40 | -8 | 5.88E-6 | 6.76E-5 | > 1.00E-4 |
| Non-Small Cell Lung Cancer | | | | | | | | | | | | | | | |
| A549/ATCC | 0.266 | 1.396 | 1.372 | 1.380 | 1.392 | 0.778 | 0.115 | 98 | 99 | 100 | 45 | -57 | 8.20E-6 | 2.77E-5 | 8.55E-5 |
| EKVX | 0.544 | 1.579 | 1.493 | 1.453 | 1.341 | 1.030 | 0.514 | 92 | 88 | 77 | 47 | -6 | 7.93E-6 | 7.85E-5 | > 1.00E-4 |
| HOP-62 | 0.378 | 1.215 | 1.184 | 1.142 | 1.074 | 0.541 | 0.190 | 96 | 91 | 83 | 19 | -50 | 3.32E-6 | 1.91E-5 | > 1.00E-4 |
| HOP-92 | 0.533 | 0.964 | 0.947 | 0.910 | 0.822 | 0.581 | 0.397 | 96 | 87 | 67 | 11 | -26 | 2.02E-6 | 2.01E-5 | > 1.00E-4 |
| NCI-H226 | 0.759 | 1.585 | 1.547 | 1.561 | 1.516 | 1.170 | 0.596 | 95 | 97 | 92 | 50 | -21 | 9.84E-6 | 4.99E-5 | > 1.00E-4 |
| NCI-H23 | 0.616 | 1.986 | 1.910 | 1.869 | 1.889 | 0.921 | 0.156 | 94 | 91 | 93 | 22 | -74 | 4.05E-6 | 1.70E-5 | 5.60E-5 |
| NCI-H322M | 0.648 | 1.620 | 1.612 | 1.526 | 1.431 | 1.061 | 0.604 | 99 | 90 | 81 | 42 | -7 | 6.33E-6 | 7.26E-5 | > 1.00E-4 |
| NCI-H460 | 0.130 | 1.291 | 1.311 | 1.256 | 1.183 | 0.241 | 0.035 | 102 | 97 | 91 | 10 | -73 | 3.17E-6 | 1.30E-5 | 5.22E-5 |
| NCI-H522 | 0.869 | 2.182 | 2.036 | 1.933 | 1.793 | 0.868 | 0.327 | 89 | 81 | 70 | . | -62 | 1.94E-6 | 9.94E-6 | 6.31E-5 |
| Colon Cancer | | | | | | | | | | | | | | | |
| COLO 205 | 0.177 | 0.746 | 0.762 | 0.673 | 0.646 | 0.204 | 0.018 | 103 | 87 | 82 | 5 | -90 | 2.61E-6 | 1.12E-5 | 3.79E-5 |
| HCC-2998 | 0.767 | 1.567 | 1.434 | 1.477 | 1.477 | 0.711 | 0.028 | 83 | 89 | 89 | -7 | -97 | 2.53E-6 | 8.39E-6 | 3.01E-5 |
| HCT-116 | 0.182 | 1.344 | 1.295 | 1.259 | 1.032 | 0.371 | 0.029 | 96 | 93 | 73 | 16 | -84 | 2.55E-6 | 1.45E-5 | 4.56E-5 |
| HCT-15 | 0.202 | 1.132 | 1.036 | 1.034 | 0.821 | 0.451 | 0.088 | 90 | 89 | 67 | 27 | -56 | 2.60E-6 | 2.10E-5 | 8.37E-5 |
| HT29 | 0.246 | 1.651 | 1.680 | 1.566 | 1.668 | 1.007 | 0.067 | 102 | 94 | 101 | 54 | -65 | 1.08E-5 | 2.86E-5 | 7.53E-5 |
| KM12 | 0.437 | 1.792 | 1.746 | 1.878 | 1.704 | 0.749 | 0.128 | 97 | 106 | 94 | 23 | -71 | 4.15E-6 | 1.75E-5 | 5.95E-5 |
| SW-620 | 0.178 | 1.084 | 1.115 | 1.053 | 1.024 | 0.493 | 0.069 | 103 | 97 | 93 | 35 | -61 | 5.49E-6 | 2.30E-5 | 7.64E-5 |
| CNS Cancer | | | | | | | | | | | | | | | |
| SF-268 | 0.412 | 1.203 | 1.146 | 1.148 | 1.023 | 0.567 | 0.305 | 93 | 93 | 77 | 18 | -26 | 2.90E-6 | 2.59E-5 | > 1.00E-4 |
| SF-295 | 0.843 | 2.453 | 2.202 | 2.320 | 2.111 | 1.203 | 0.484 | 84 | 92 | 79 | 22 | -43 | 3.23E-6 | 2.21E-5 | > 1.00E-4 |
| SF-539 | 0.693 | 2.196 | 2.093 | 2.041 | 1.830 | 0.733 | 0.257 | 93 | 90 | 76 | 3 | -63 | 2.24E-6 | 1.10E-5 | 6.34E-5 |
| SNB-19 | 0.361 | 1.295 | 1.258 | 1.215 | 1.100 | 0.533 | 0.310 | 96 | 91 | 79 | 18 | -14 | 3.02E-6 | 3.68E-5 | > 1.00E-4 |
| SNB-75 | 0.442 | 0.908 | 0.843 | 0.825 | 0.729 | 0.503 | 0.409 | 86 | 82 | 61 | 13 | -8 | 1.72E-6 | 4.28E-5 | > 1.00E-4 |
| U251 | 0.195 | 1.025 | 1.070 | 0.953 | 0.644 | 0.316 | 0.146 | 105 | 93 | 54 | 15 | -25 | 1.27E-6 | 2.32E-5 | > 1.00E-4 |
| Melanoma | | | | | | | | | | | | | | | |
| LOX IMVI | 0.290 | 1.644 | 1.606 | 1.533 | 1.333 | 0.582 | 0.053 | 97 | 92 | 77 | 22 | -82 | 3.07E-6 | 1.62E-5 | 4.92E-5 |
| MALME-3M | 0.681 | 1.286 | 1.281 | 1.263 | 1.180 | 0.969 | 0.619 | 99 | 96 | 82 | 46 | -9 | 7.73E-6 | 6.83E-5 | > 1.00E-4 |
| M14 | 0.371 | 1.179 | 1.116 | 1.099 | 1.016 | 0.542 | 0.093 | 92 | 90 | 80 | 21 | -75 | 3.23E-6 | 1.86E-5 | 5.49E-5 |
| MDA-MB-435 | 0.465 | 1.697 | 1.655 | 1.619 | 1.426 | 0.647 | 0.295 | 97 | 94 | 78 | 15 | -37 | 2.77E-6 | 1.94E-5 | > 1.00E-4 |
| SK-MEL-2 | 0.945 | 1.785 | 1.729 | 1.768 | 1.588 | 0.937 | 0.293 | 93 | 98 | 77 | -1 | -69 | 2.20E-6 | 9.74E-6 | 5.25E-5 |
| SK-MEL-28 | 0.418 | 1.109 | 1.105 | 1.069 | 1.084 | 0.639 | 0.117 | 99 | 94 | 96 | 32 | -72 | 5.24E-6 | 2.03E-5 | 6.13E-5 |
| SK-MEL-5 | 0.362 | 1.880 | 1.857 | 1.783 | 1.461 | 0.458 | -0.003 | 98 | 94 | 72 | 6 | -100 | 2.18E-6 | 1.14E-5 | 3.38E-5 |
| UACC-257 | 0.722 | 1.555 | 1.519 | 1.526 | 1.502 | 1.159 | 0.462 | 96 | 96 | 94 | 52 | -36 | 1.06E-5 | 3.91E-5 | > 1.00E-4 |
| UACC-62 | 0.766 | 2.122 | 2.009 | 1.979 | 1.892 | 0.774 | 0.118 | 92 | 89 | 83 | 1 | -85 | 2.52E-6 | 1.02E-5 | 3.92E-5 |
| Ovarian Cancer | | | | | | | | | | | | | | | |
| IGROV1 | 0.232 | 0.878 | 0.797 | 0.814 | 0.686 | 0.220 | 0.094 | 87 | 90 | 70 | -5 | -59 | 1.86E-6 | 8.54E-6 | 6.69E-5 |
| OVCAR-3 | 0.339 | 0.881 | 0.893 | 0.889 | 0.766 | 0.316 | 0.085 | 102 | 101 | 78 | -7 | -75 | 2.16E-6 | 8.30E-6 | 4.29E-5 |
| OVCAR-4 | 0.452 | 1.371 | 1.329 | 1.326 | 1.115 | 0.706 | 0.434 | 95 | 95 | 72 | 28 | -4 | 3.14E-6 | 7.48E-5 | > 1.00E-4 |
| OVCAR-5 | 0.538 | 1.130 | 1.117 | 1.070 | 1.077 | 0.787 | 0.230 | 98 | 90 | 91 | 42 | -57 | 6.89E-6 | 2.65E-5 | 8.45E-5 |
| OVCAR-8 | 0.592 | 1.952 | 1.919 | 1.928 | 1.836 | 0.764 | 0.345 | 98 | 98 | 91 | 13 | -42 | 3.38E-6 | 1.71E-5 | > 1.00E-4 |
| NCI/ADR-RES | 0.563 | 1.658 | 1.700 | 1.621 | 1.657 | 1.166 | 0.548 | 104 | 97 | 100 | 55 | -3 | 1.22E-5 | 8.96E-5 | > 1.00E-4 |
| SK-OV-3 | 0.476 | 1.167 | 1.156 | 1.178 | 1.139 | 0.804 | 0.192 | 99 | 101 | 96 | 47 | -60 | 6.80E-6 | 2.76E-5 | 8.10E-5 |
| Renal Cancer | | | | | | | | | | | | | | | |
| 786-0 | 0.523 | 1.735 | 1.708 | 1.636 | 1.432 | 0.739 | 0.221 | 98 | 92 | 75 | 18 | -58 | 2.73E-6 | 1.72E-5 | 7.90E-5 |
| A498 | 0.770 | 1.553 | 1.424 | 1.454 | 1.574 | 1.012 | 0.377 | 84 | 87 | 103 | 31 | -51 | 5.42E-6 | 2.38E-5 | 9.71E-5 |
| ACHN | 0.375 | 1.525 | 1.533 | 1.505 | 1.359 | 0.695 | 0.303 | 101 | 98 | 86 | 28 | -19 | 4.13E-6 | 3.91E-5 | > 1.00E-4 |
| CAKI-1 | 0.430 | 0.748 | 0.659 | 0.730 | 0.689 | 0.607 | 0.324 | 72 | 94 | 81 | 56 | -25 | 1.18E-5 | 4.92E-5 | > 1.00E-4 |
| SN12C | 0.375 | 1.151 | 1.155 | 1.087 | 1.044 | 0.647 | 0.267 | 100 | 92 | 86 | 35 | -29 | 5.10E-6 | 3.53E-5 | > 1.00E-4 |
| TK-10 | 0.611 | 1.369 | 1.298 | 1.229 | 1.186 | 0.850 | 0.543 | 91 | 82 | 76 | 31 | -11 | 3.82E-6 | 5.48E-5 | > 1.00E-4 |
| UO-31 | 0.343 | 0.913 | 0.861 | 0.834 | 0.678 | 0.390 | 0.140 | 91 | 86 | 58 | 8 | -59 | 1.47E-6 | 1.32E-5 | 7.28E-5 |
| Prostate Cancer | | | | | | | | | | | | | | | |
| PC-3 | 0.207 | 1.193 | 1.210 | 1.174 | 1.048 | 0.566 | 0.215 | 102 | 98 | 85 | 37 | 1 | 5.31E-6 | > 1.00E-4 | > 1.00E-4 |
| DU-145 | 0.304 | 1.019 | 1.068 | 1.088 | 0.979 | 0.550 | 0.148 | 107 | 110 | 94 | 34 | -51 | 5.48E-6 | 2.51E-5 | 9.61E-5 |
| Breast Cancer | | | | | | | | | | | | | | | |
| MCF7 | 0.173 | 1.081 | 1.031 | 0.977 | 0.840 | 0.372 | 0.056 | 94 | 89 | 73 | 22 | -68 | 2.85E-6 | 1.75E-5 | 6.32E-5 |
| MDA-MB-231/ATCC | 0.526 | 1.199 | 1.240 | 1.152 | 1.047 | 0.783 | 0.481 | 106 | 93 | 77 | 38 | -9 | 4.99E-6 | 6.58E-5 | > 1.00E-4 |
| HS 578T | 0.483 | 0.914 | 0.879 | 0.869 | 0.800 | 0.528 | 0.419 | 92 | 90 | 74 | 10 | -13 | 2.36E-6 | 2.73E-5 | > 1.00E-4 |
| BT-549 | 0.968 | 1.842 | 1.742 | 1.683 | 1.600 | 1.077 | 0.728 | 89 | 82 | 72 | 12 | -25 | 2.36E-6 | 2.16E-5 | > 1.00E-4 |
| T-47D | 0.467 | 1.135 | 1.110 | 1.050 | 0.956 | 0.555 | 0.345 | 96 | 87 | 73 | 13 | -26 | 2.43E-6 | 2.16E-5 | > 1.00E-4 |
| MDA-MB-468 | 0.279 | 0.632 | 0.588 | 0.582 | 0.531 | 0.390 | 0.117 | 88 | 86 | 71 | 31 | -58 | 3.42E-6 | 2.24E-5 | 8.09E-5 |

RIBONUCLEOTIDE REDUCTASE INHIBITORS AND METHODS OF USE

RELATED APPLICATIONS

This application is a continuation of U.S. application Ser. No. 15/418,366, filed Jan. 27, 2017, which is a divisional of U.S. application Ser. No. 14/754,100, filed Jun. 29, 2015, now U.S. Pat. No. 9,598,385, which is a continuation of U.S. application Ser. No. 14/444,172, filed Jul. 28, 2014, now U.S. Pat. No. 9,126,960, which is a continuation of International Application No. PCT/US2013/024490, filed Feb. 1, 2013, which claims the benefit of U.S. application Ser. No. 13/364,263, filed Feb. 1, 2012, now U.S. Pat. No. 8,372,983, the disclosure of each of which is incorporated by reference herein in its entirety for all purposes.

GOVERNMENT INTEREST

This invention was made with Government support under grant number CA127541 awarded by the National Institutes of Health. The Government has certain rights in this invention.

BACKGROUND

Ribonucleotide diphosphate reductase (RR) is a highly regulated enzyme in the deoxyribonucleotide synthesis pathway that is ubiquitously present in human, bacteria, yeast, and other organisms (Jordan 1998). RR is responsible for the de novo conversion of ribonucleotide diphosphate to 2'-deoxyribonucleotide diphosphate, a process that is essential for DNA synthesis and repair (Thelander 1986; Jordan 1998; Liu 2006). RR is directly involved in tumor growth, metastasis, and drug resistance (Yen 1994; Zhou 1995; Nocentini 1996; Fan 1998; Zhou 1998).

The proliferation of metastatic cancer cells requires excess dNTPs for DNA synthesis. Therefore, an increase in RR activity is necessary as it helps provide extra dNTPs for DNA replication in primary and metastatic cancer cells. Because of this critical role in DNA synthesis, RR represents an important target for cancer therapy. However, there has been little progress in the development of RR inhibitors for use in cancer treatment. The three RR inhibitors currently in clinical use (hydroxyurea, 3-aminopyridine-2-carboxaldehyde thiosemicarbazone (3-AP), and GTI2040) each have significant drawbacks. Therefore, there is a need in the art for more effective compositions and methods for targeting and treating RR-based cancers.

SUMMARY

In certain embodiments, a novel set of compounds including COH4, COH20, and COH29, as well as various chemical derivatives thereof, are provided. Also provided are compositions and pharmaceutical formulations comprising these compounds.

In certain embodiments, methods are provided for inhibiting RR activity in a cell by contacting the cell with one or more of the compounds provided herein, including COH4, COH20, and/or COH29.

In certain embodiments, methods are provided for inhibiting the growth or proliferation of a cell expressing RRM2 by contacting the cell with a therapeutically effective amount of one or more of the compounds provided herein, including COH4, COH20, and/or COH29.

In certain embodiments, methods are provided for treating cancer in a subject in need thereof by administering a therapeutically effective amount of one or more of the compounds provided herein, including COH4, COH20, and/or COH29. In certain embodiments, the cancer may be characterized by RRM2 overexpression, and in certain embodiments the cancer may be resistant to treatment with hydroxyurea.

In certain embodiments, methods are provided for inhibiting proliferation of a stem cell expressing RRM2 by contacting the stem cell with a therapeutically effective amount of one or more of the compounds provided herein, including COH4, COH20, and/or COH29.

In certain embodiments, a compound is provided having the formula:

Structure VIA

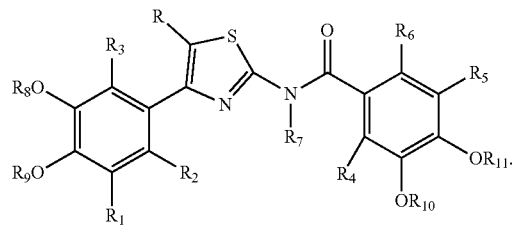

In Structure VIA, R is substituted or unsubstituted aryl. $R_1$, $R_2$, $R_3$, $R_4$, $R_5$, $R_6$, and $R_7$ are independently hydrogen, —OH, —$NH_2$, —SH, —CN, —$CF_3$, —$NO_2$, oxo, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R_8$, $R_9$, $R_{10}$ and $R_{11}$ are independently a hydroxyl protecting group. $R_8$ and $R_9$ are optionally joined together to form a substituted or unsubstituted heterocycloalkyl. $R_{10}$ and $R_{11}$ are optionally joined together to form a substituted or unsubstituted heterocycloalkyl.

In certain embodiments, a composition is provided including the compound of Structure VIA or embodiments thereof and an organic solvent (e.g. a non-polar solvent of a polar aprotic solvent).

In certain embodiments, a composition is provided including the compound of Structure VIA or embodiments thereof and a hydroxyl deprotecting agent.

In certain embodiments, a method is provided for synthesizing a compound having the structure:

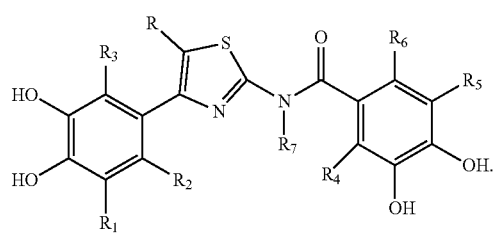

The method includes contacting a hydroxyl deprotecting agent with a compound having the formula:

Structure VIA

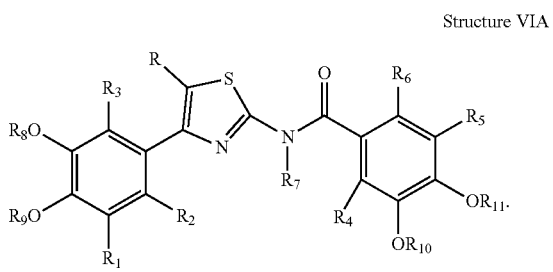

The $R_8$, $R_9$, $R_{10}$ and $R_{11}$ deprotecting groups are thereby removed. In Structure VIA, R is substituted or unsubstituted aryl. $R_1$, $R_2$, $R_3$, $R_4$, $R_5$, $R_6$, and $R_7$ are independently hydrogen, —OH, —$NH_2$, —SH, —CN, —$CF_3$, —$NO_2$, oxo, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R_8$, $R_9$, $R_{10}$ and $R_{11}$ are independently a hydroxyl protecting group. $R_8$ and $R_9$ are optionally joined together to form a substituted or unsubstituted heterocycloalkyl. $R_{10}$ and $R_{11}$ are optionally joined together to form a substituted or unsubstituted heterocycloalkyl.

In certain embodiments, methods are provided for the synthesis and/or purification of various compounds disclosed herein, including COH4, COH20, and/or COH29. In certain embodiments, methods are provided for synthesizing and/or purifying COH29 or various COH29 synthesis intermediates. In certain of these embodiments, the synthesis methods provided herein utilize veratrole as a starting material, and in certain of these embodiments COH29 synthesis is accomplished via 1-(3,4-dimethoxyphenyl)-2-phenylethanone, 4-(3,4-dimethoxyphenyl)-5-phenylthiazol-2-amine, and N-(4-(3,4-dimethoxyphenyl)-5-phenylthiazol-2-yl)-3,4-dimethoxybenzamide intermediates. In certain of these embodiments, synthesis of COH29 proceeds via the following synthesis pathway:

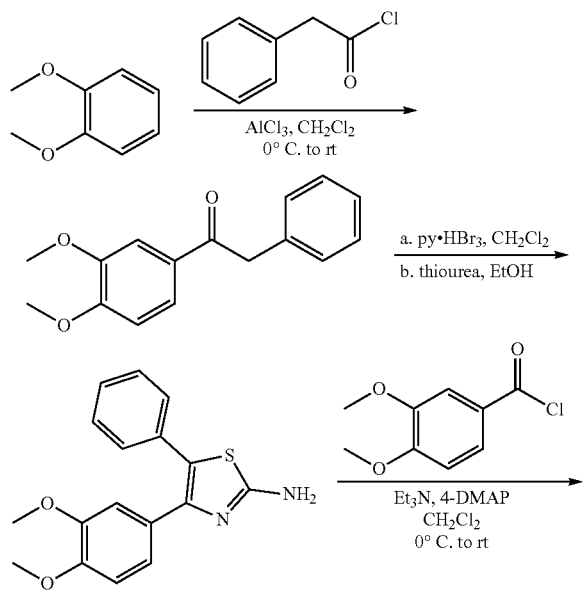

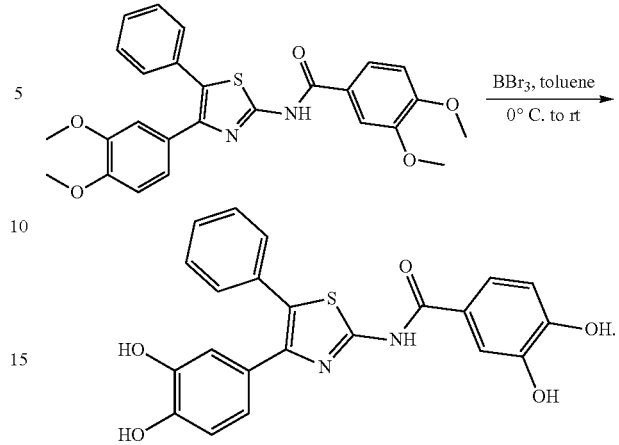

BRIEF DESCRIPTION OF THE DRAWINGS

FIG. 1A: HP TV injection of female BALB/c Mice with pR2Luc. FIG. 1B: Images taken 2-days post-injection, all at same scale.

FIG. 2A: Histogram of M2 mRNA expression level in normal (N) and breast cancer tissue (Y). FIG. 2B: Figure depicts Western blot which revealed that normal human tissues other than fetal liver and testis express low levels of RRM2, whereas cancer cells express significantly higher levels of RRM2.

FIGS. 3A-3C: RRM2 transfectant enhances invasive potential in human cancer cell lines. Human oropharyngeal cancer KB (wild-type p53) and human prostate cancer PC3 (truncated p53) cells were transfected with sense RRM2 (KBM2 and PC3M2, respectively) and control vector, and the resulting overexpression of RRM2 was confirmed by Western blot analysis (FIG. 3A). Transfectants were applied to the upper layer of MATRIGEL® in a Borden chamber. After 72 hours, cells that invaded to the lower layer were fixed with alcohol, stained with methylene blue, and counted and examined (FIG. 3B). FIG. 3C: Comparison of RR expression and migration ability of Vector and RRM2 sense transfectants.

FIGS. 15E-15H: Annexin staining of KB cells following treatment with 3-AP or COH20 at indicated concentrations.

FIG. 23: Inhibition of cancer cell growth by multiple-dose administration of COH29.

DETAILED DESCRIPTION

Figure 1A:
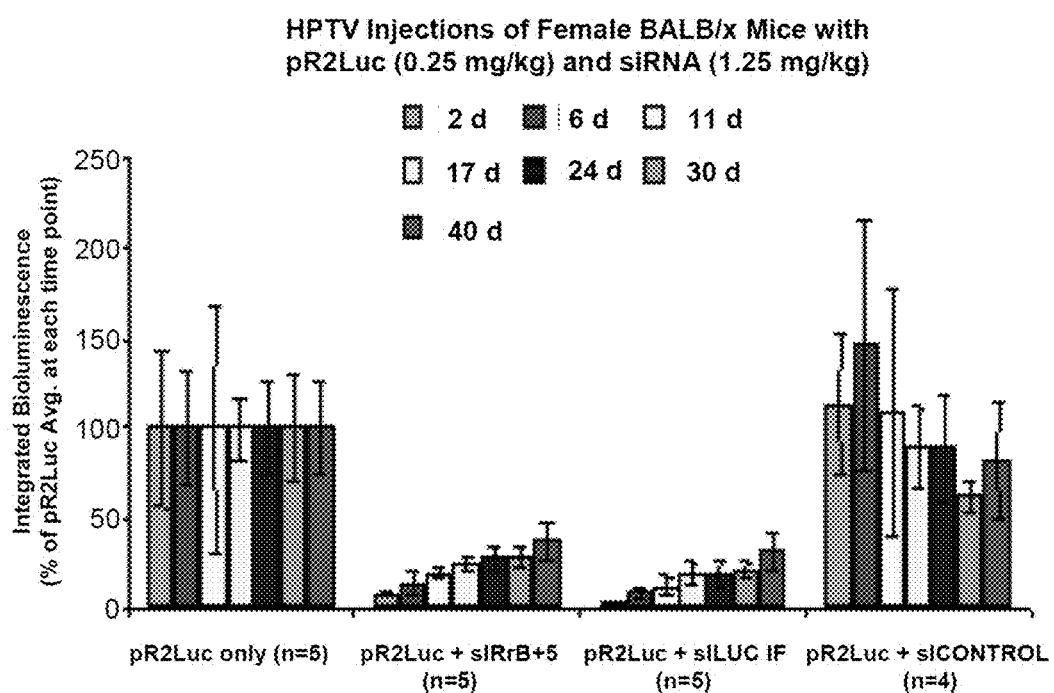
FIGS. 1A-1B: Suppression of RRM2 via siRNA in mice implanted with human HepG2 liver cancer cells decreases tumor growth.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

The following abbreviations are used herein: 3-AP, 3-aminopyridine-2-carboxaldehyde thiosemicarbazone; DCM, dichloromethane; DMF, dimethylformamide; dNTP, deoxyribonucleotide triphosphate; HU, hydroxyurea; RR, ribonucleotide reductase; RRM1, ribonucleotide reductase large subunit; RRM2, ribonucleotide reductase small subunit.

The phrase "therapeutically effective amount" as used herein refers to an amount of a compound that produces a desired therapeutic effect. The precise therapeutically effective amount is an amount of the composition that will yield the most effective results in terms of efficacy in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy (Gennaro ed. 20$^{th}$ edition, Williams & Wilkins PA, USA) (2000).

"Treating" or "treatment" of a condition as used herein may refer to preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic and/or malignant cell growth, proliferation, and/or metastasis, preventing or delaying the development of neoplastic and/or malignant cell growth, proliferation, and/or metastasis, or some combination thereof. With regard to a tumor, "treating" or "treatment" may refer to eradicating all or part of a tumor, inhibiting or slowing tumor growth and metastasis, preventing or delaying the development of a tumor, or some combination thereof.

A cancer "characterized by overexpression of RRM2" as used herein refers to any cancer type that expresses RRM2 at either the mRNA or protein level at a level greater than that of a corresponding normal cell or tissue. For example, a prostate cancer cell line is a cancer characterized by overexpression of RRM2 if it expresses RRM2 at either the mRNA or protein level at a level greater than that observed in a corresponding normal prostate cell. A cancer characterized by overexpression of RRM2 as used herein also refers to any cancer type in which RRM2 inhibitors exhibit additional or selective effects compared to normal, untransformed cells or tissues. For example, a cancer type is a cancer characterized by RRM2 overexpression if it has a greater dependency on the nucleotide pool because of a difference in mitotic indices with normal cells, making it more sensitive to RRM2 inhibition.

As used herein, the term "hydroxyl protecting group" is a monovalent chemical moiety covalently bound to a monovalent hydroxyl oxygen atom that functions to prevent the hydroxyl moiety from reacting with reagents used in the chemical synthetic methods described herein (commonly referred to as "protecting" the hydroxyl group) and may be removed under conditions that do not degrade the molecule of which the hydroxyl moiety forms a part (commonly referred to as "deprotecting" the hydroxyl group) thereby yielding a free hydroxyl. A hydroxyl protecting group can be acid labile, base labile, or labile in the presence of other reagents. Hydroxyl protecting groups include but are not limited to activated ethylene protecting group, a benzyl ether protecting group, a silicon-based carbonate protecting group, an acetal protecting group or a cyclic acetal protecting group. Hydroxyl protecting groups include methyl benzyl, p-methoxybenzyl, allyl, trityl, p-methoxyphenyl, tetrahydropyranyl, methoxymethyl, 1-ethoxyethyl, 2-methoxy-2-propy, 2,2,2-trichloroethoxymethyl, 2-methoxyethoxymethyl, 2-trimethylsilylethoxymethyl, methylthiomethyl, trimethylsilyl, triethylsilyl, triisopropylsilyl, triphenylsilyl, t-butyldimethylsilyl, t-butyldiphenylsilyl,

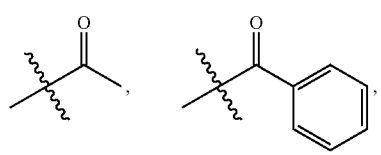

-continued

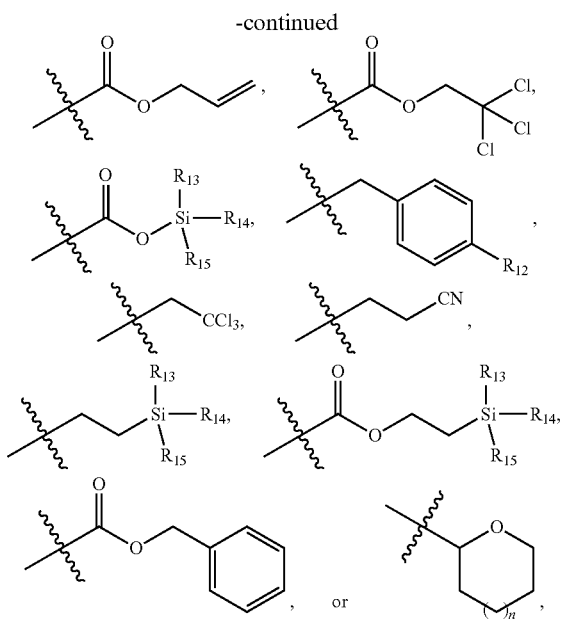

wherein n is 0 or 1; $R_{12}$ is hydrogen, —OH, —OR$_{16}$ or substituted or unsubstituted alkyl, wherein Rib is substituted or unsubstituted alkyl; and $R_{13}$, $R_{14}$ and $R_{15}$ are substituted or unsubstituted alkyl.

As used herein, the term "hydroxyl deprotecting agent" is a chemical compound or element that functions to remove a hydroxyl protecting group, thereby yielding a free hydroxyl. Hydroxyl deprotecting agents useful in the present methods include: zinc bromide, magnesium bromide, titanium tetrachloride, dimethylboron bromide, trimethylsilyl iodide, silver (Ag+) salts, mercury (Hg+) salts, zinc, samarium diiodide, sodium amalgam, trifluoroacetic acid, hydrofluoric acid, hydrochloric acid, hydrogenation, (TBAF) tetra-n-butylammonium fluoride, boron trifluoride, silicon tetrafluoride, boron tribromide, an aryl methyl ether, tetrabutylammonium fluoride, hydrogen/Pd/C, Zn/acid or ammonia.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. Non-limiting examples of heteroaryl groups include pyridinyl, pyrimidinyl, thiophenyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

Each of the above terms (e.g., "alkyl," "heteroalkyl," "aryl," and "heteroaryl") includes both substituted and unsubstituted forms (as indicated herein) of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SW, -halogen, —SiR'R"R'", —OC(O)R', —C(O)R', —CO$_2$R', —CONR'R", —OC(O)NR'R", —NR"C(O)R', —NR"C(O)NR'R", —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:
  (i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and/or each substituted or unsubstituted heterocycloalkyl is a substituted or unsubstituted 5 to 7 membered heterocycloalkyl.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

The symbol ⟿ represents the point of attachment of a substituent to the remainder of the compound.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

dNTP production in eukaryotes is tightly regulated by RR, which catalyzes the rate-limiting step in deoxyribonucleotide synthesis (Jordan 1998). RR consists of a large subunit and a small subunit. In humans, one large subunit (RRM1, also referred to as M1) and two small subunits (RRM2, also referred to as M2, and p53R2) have been identified (Tanaka 2000; Liu 2006). The small RR subunits form two equivalent dinuclear iron centers that stabilize the tyrosyl free radical required for initiation of electron transformation during catalysis (Ochiai 1990; Cooperman 2003; Liu 2006).

RRM1 is a 170 Kd dimer containing substrate and allosteric effector sites that control RR holoenzyme activity and substrate specificity (Cory 1983; Wright 1990; Cooperman 2003; Liu 2006).

RRM2 is an 88 Kd dimer containing a tyrosine free radical and a non-heme iron for enzyme activity (Chang 1979). p53R2 contains a p53-binding site in intron 1 and encodes a 351-amino-acid peptide with striking similarity to RRM2 (Tanaka 2000). RRM2 and p53R2 have an 80% similarity in amino acid sequence (Tanaka 2000).

p53R2 has been identified as a transcriptional target of p53 (Nakano 2000; Tanaka 2000; Yamaguchi 2001), while RRM2 is transcriptionally regulated by cell cycle-associated factors such as NF-Y and E2F (Filatov 1995; Currie 1998; Chabes 2004; Liu 2004). Therefore, expression of p53R2, but not RRM2, is induced by ultraviolet (UV) light, gamma-irradiation, or Doxorubicin (Dox) treatment in a p53-dependent manner (Lozano 2000; Tanaka 2000; Guittet 2001). In p53 mutant or deleted cells, RRM2 can replace p53R2 in the DNA repair process for cells exposed to UV irradiation (Zhou 2003; Liu 2005). P53R2 has been found to have a stronger reducing capacity than RRM2, which may provide a chaperone effect in stabilizing p21 (Xue 2007).

It has been observed that the RB tumor suppressor suppresses RR subunits as a mechanism for regulating cell cycle progression (Elledge 1990). RB inactivation, often observed in tumors, leads to increased dNTP levels and a concomitant resistance of tumor cells to drugs such as 5-fluorouracil (5-Fu) and HU (Angus 2002). While overexpression of the RRM2 subunit promotes transformation and tumorigenic potential via its cooperation with several activated oncogenes (Fan 1998), overexpression of the RRM1 subunit suppresses malignant potential in vivo (Fan 1997). Increased expression of RRM2 has been found to increase the drug-resistant properties of cancer cells and to increase invasive potential, whereas RRM2 suppression leads to the reversal of drug resistance and results in decrease proliferation of tumor cells (Zhou 1995; Huang 1997; Zhou 1998; Goan 1999; Chen 2000; Nakano 2000; Kuschak 2002). Normal cells express very low levels of RR in non-proliferative status, whereas most neoplastic cells overexpress RR, thereby supplying dNTP pools for DNA synthesis and cell proliferation. Thus, specific inhibition of RRM2 is likely to provide antineoplastic benefits.

Although RR represents an important target for cancer therapy, there are only three RR inhibitors in clinical use: hydroxyurea (HU), 3-aminopyridine-2-carboxaldehyde thiosemicarbazone (3-AP, TRIAPINE®), and GTI2040. HU, which blocks DNA synthesis by reducing the tyrosyl free radical, has been marketed as a cancer therapeutic for over 30 years and is the only RR inhibitor that is commercially available (Nocentini 1996). However, resistance to HU treatment is a common problem (Lassmann 1992; Nyholm 1993; Le 2002). 3-AP, a small molecule iron chelator inactivates RR, has been found to cause hypoxia, respiratory distress, and methemoglobulin of red blood cells. In addition, 3-AP selectively targets p53R2 instead of RRM2. GTI2040, an antisense molecule, has thus far been ineffective in human trials. Other issues relating to these three RR inhibitors are incomplete RR blocking, short half-life, and regeneration of RR. In addition, mutation of p53R2 results in hereditary mitochondria depletion syndrome, but not cancer, and p53R2 knockout mice demonstrate kidney tubule disorder but no obvious cancer growth (Kimura 2003). These observations suggest that RRM2 is responsible for tumor proliferation and metastatic potential, whereas p53R2 induced by DNA damage signals for DNA repair. Therefore, an ideal RR inhibitor for use in cancer therapy would have greater potency than HU, less iron chelating ability than 3-AP, and specific targeting of RRM2.

As disclosed herein, RRM2 has been validated as an anti-cancer target. Suppression of RRM2 via siRNA was found to decrease tumor growth in mice implanted with human HepG2 liver cancer cells. Expression of RRM2 was determined to be significantly higher in cancer cells than in corresponding normal cells. In addition, human KB and PC3 cells transfected with RRM2 exhibited increased invasive potential versus their non-transfected counterparts, suggesting that RRM2 enhances the invasive potential of cancer cells.

A diverse compound library from NCI Developmental Therapeutics Program (DTP) was screened to identify compounds that inhibit RR. Three of the four compounds identified in this screen that inhibited RRM1/RRM2 activity by 80% of more shared a similar structural scaffold, NCI-3. NCI-3 has the structure:

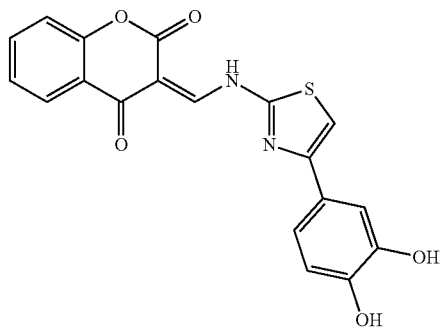 [SMILES: O=C1Oc2ccccc2C(=O)/C1=C/Nc1nc(-c2ccc(O)c(O)c2)cs1]

Initial hits from the screening process were synthetically and rationally optimized to obtain the RR inhibitors COH1, COH2, COH4, COH20, and COH29, the structures of which are set forth below.

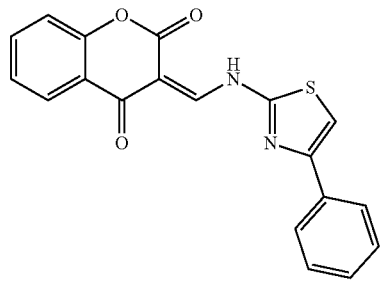
COH1:

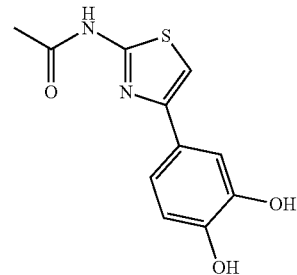
COH2:

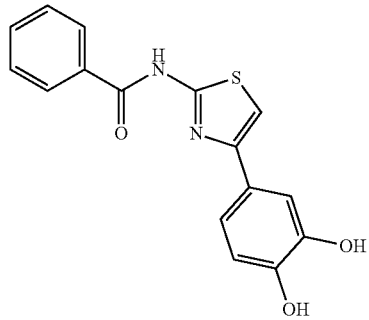
COH4:

-continued

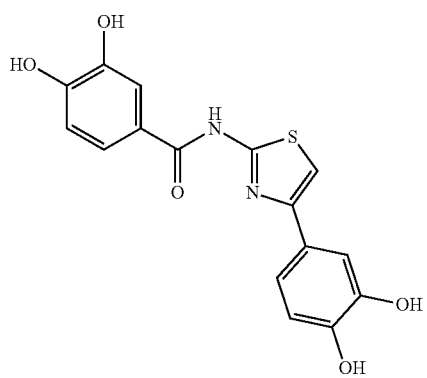

COH20:

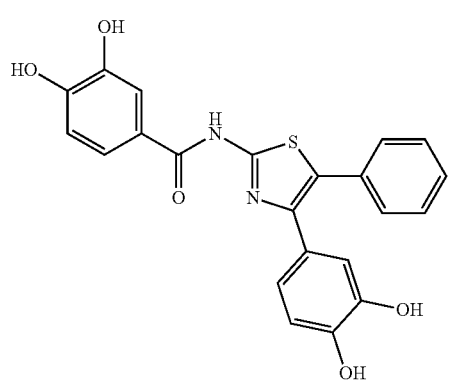

COH29

(N-(4-(3,4-dihydroxyphenyl)-5-phenylthiazol-2-yl)-3,4-dihydroxybenzamide):

Each of these compounds exhibited the ability to inhibit RR to a significant degree, and COH20 and COH29 both exhibited the ability to inhibit cancer cell growth across a wide range of cancer cell types. Accordingly, in certain embodiments the present application discloses novel RR inhibitors, compositions, formulations, and kits comprising one or more of these inhibitors, and methods of using these inhibitors to inhibit RR, inhibit cell growth or proliferation, treat cancer, and/or inhibit stem cell proliferation.

COH20 consists of three basic structural units: a pharmacophore (for inhibition of RR activity), a binding group (for selectivity), and a linking group (to connect the pharmacophore and the binding group. As disclosed herein, COH20 exhibited low micromolar range inhibition of both recombinant and intracellular RR in vitro, and caused a decrease in dNTP pools. Biochemical analysis revealed that COH20 targets RRM2. Upon binding the RRM1/RRM2 complex, COH20 appears to reside at the V-shaped pocket at the interface between RRM1 and RRM2 and block the free radical transfer pathway though a novel catechol radical stabilization mechanism. Considering the size and chemical composition of COH20 and the distance to the dinuclear iron center, the bound ligand (in this pocket) does not appear to be susceptible to iron chelation as with 3-AP or involved in the direct quenching of the initially formed tyrosyl free radical as with HU. COH20 was found to inhibit growth of the human leukemia cell lines REH and MOLT-4, the human prostate cancer cell line LNCaP, and the human oropharyngeal cancer cell line KB in vitro at a concentration of less than 10 μM, while exhibiting less cytotoxicity towards normal fibroblast cells than HU. COH20 also exhibited greater cytotoxicity towards the HU-resistant cell line KBHURs than 3-AP, indicating that it is capable of overcoming HU drug resistance. COH20 exhibited cytotoxicity towards KBMDR cells at lower concentration than 3-AP or HU (80 μM versus 200 μM and >1000 μM, respectively), indicating that COH20 circumvents MDR more effectively than 3-AP. In addition, COH20 had very low toxicity when administered to mice, with no evidence or iron chelation or methemoglobulin.

As disclosed herein, COH29 showed promising growth inhibitory effects on a wide range of human cancer cell lines, including:

human non-small cell lung cancer cell lines NCI-H23, NCI-H522, A549-ATCC, EKVX, NCI-H226, NCI-H332M, H460, H0P62, HOP92;

human colon cancer cell lines HT29, HCC-2998, HCT116, SW620, COLO205, HCT15, KM12;

breast cancer cell lines MCF7, MCF7ADRr, MDAMB231, HS578T, MDAMB435, MDN, BT549, T47D;

ovarian cancer cell lines OVCAR3, OVCAR4, OVCAR5, OVCAR8, IGROV1, SKOV3;

human leukemia cell lines CCRFCEM, K562, MOLT4, HL60, RPMI8266, SR;

renal cancer cell lines UO31, SN12C, A498, CAKI1, RXF393, 7860, ACHN, TK10;

melanoma cell lines LOXIMVI, MALME3M, SKMEL2, SKMEL5, SKMEL28, M14, UACC62, UACC257;

prostate cancer cell lines PC3, DU145; and

CNS cancer cell lines SNB19, SNB75, U251, SF268, SF295, SM539.

In certain embodiments, COH29 showed a GI50 of less than about 10 μM for the NCI 60 human cancer cell lines, except colon cancer cell line HT29, melanoma cancer cell line UACC-257, ovarian cancer cell line NCI/ADR-RES, and renal cancer cell line CAKI-1. In addition, pharmacokinetic studies of COH29 showed a dose-dependent manner when COH29 was administered by i.v. bolus.

COH4, COH20 and COH29 represent unique RR inhibitors with high antitumoral activity that provide significant advantages over previously disclosed RR inhibitors. Specifically, COH20 offers a unique mechanism and target specificity that interferes with the radical transfer pathway at the RRM1/RRM2 interface with greater potency than HU and amelioration of the iron chelation-related side effects observed with 3-AP. Therefore, provided herein in certain embodiments are small molecule RR inhibitors and methods of using these inhibitors to inhibit RR and to treat cancer. The inhibitors disclosed herein are capable of overcoming HU resistance, a common obstacle to cancer therapy, and are also capable of overcoming multidrug resistance.

In certain embodiments, a novel RR inhibitor as disclosed herein is COH1, COH2, COH4, COH20, or COH29, or a pharmaceutically acceptable salt, solvate, stereoisomer, or prodrug derivative thereof.

In certain embodiments, a novel RR inhibitor as disclosed herein is:

(Group 1)

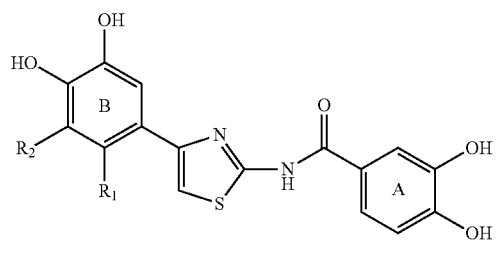

COH20.1

R$_1$, R$_2$ = alkyl, aryl

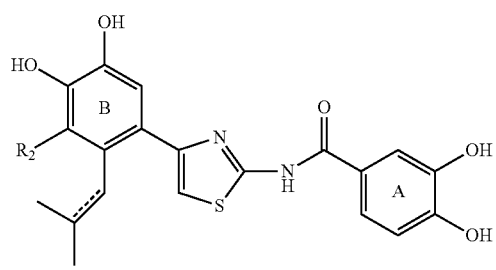

COH20.1a

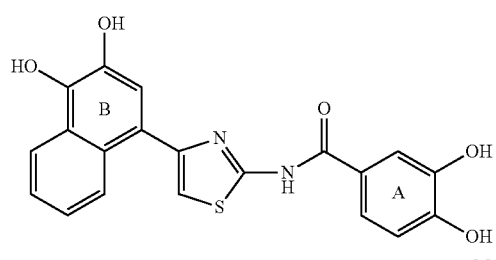

COH20.1b

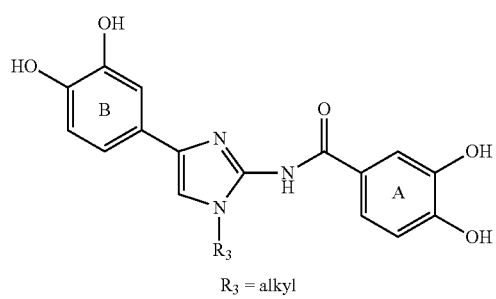

COH20.2

R$_3$ = alkyl

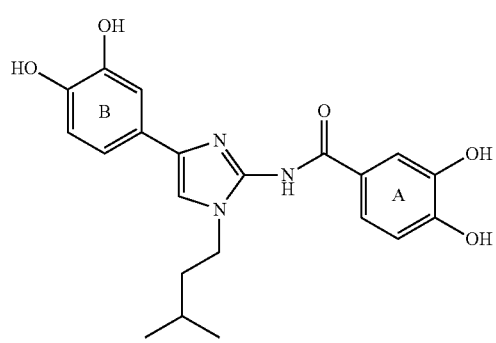

COH20.2a

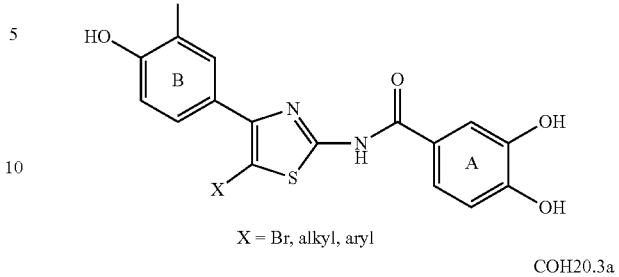

COH20.3

X = Br, alkyl, aryl

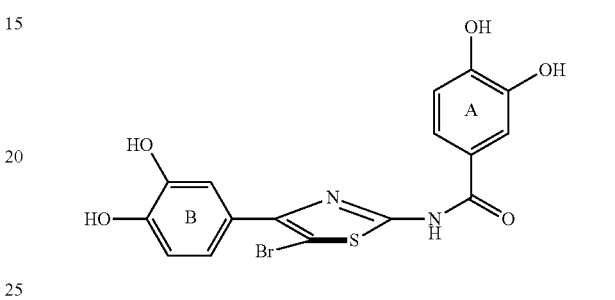

COH20.3a

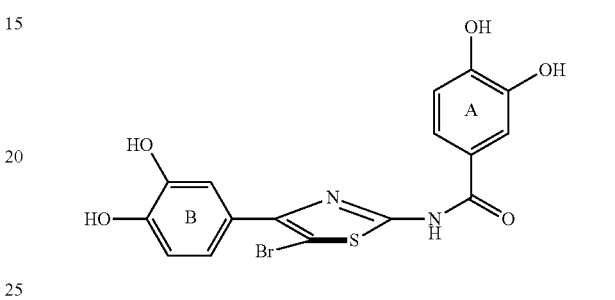

X is selected from the group consisting of halogen, substituted and unsubstituted alkyl and substituted and unsubstituted aryl groups;

R$_1$-R$_2$ are independently selected from the group consisting of H, OH, substituted and unsubstituted alkyl, and substituted and unsubstituted aryl groups; and R$_1$-R$_2$ may combine together to form a ring wherein the ring is aryl or non-aryl.

As used herein, the term "halogen" means F, Cl, Br, I and At.

The RR inhibitors disclosed herein specifically target RRM2, inhibiting the interaction between RRM1 and RRM2 and inhibiting the activity of the RR complex. Therefore, these inhibitors may be used to certain cancers, including cancers associated with the overexpression of RRM2 or for which there exists a suitable therapeutic index. As disclosed herein, RRM2 may be overexpressed in breast cancer cells versus normal cells, and expression of exogenous RRM2 increases cancer cell invasive potential. The inhibitors disclosed herein have been shown to inhibit growth of multiple cancer cell types in vitro, supporting the use of these inhibitors to treat a wide range of cancers.

Previous studies have shown that RRM2 is highly expressed in stem cells in the colon (Liu 2006). At the early stages of colon cancer, RRM2 expression decreases slightly. However, RRM2 expression increases significantly once the tumor becomes aggressive. These results support the findings herein that RRM2 expression is associated with an increase in cancer cell invasiveness. In addition, they support the use of the inhibitors disclosed herein to inhibit the growth or proliferation of stem cells giving rise to cancer, thereby preventing or slowing the onset of certain cancer types.

In addition to cancer, the inhibitors disclosed herein may be used to treat other conditions associated with RR or RR overexpression, such as for example various mitochondrial, redox-related, or degenerative diseases. In addition, the inhibitors may be used to inhibit growth or proliferation of cells expressing RR.

Provided herein in certain embodiments are methods for both small- and large-scale synthesis of the small molecule RR inhibitors disclosed herein. In certain of these embodiments, the small molecule RR inhibitor being synthesized is COH29. Small molecule RR inhibitors synthesized using the methods provided herein may be purified by various methods known in the art. Specific purification steps that may be utilized include, for example, precipitation, trituration, crystallization, or chromatographic techniques such as silica gel chromatography.

In certain embodiments, methods are provided for the synthesis of COH29. In certain of these embodiments, the starting material is a compound having the structure:

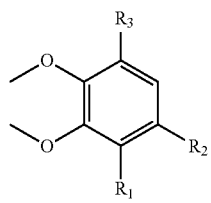

Structure II where $R_1$, $R_2$, and $R_3$ are each independently hydrogen, a substituted or unsubstituted aryl, or a substituted or unsubstituted alkyl. In certain of these embodiments, the starting material compound is veratrole (1,2-dimethoxybenzene), which has the structure:

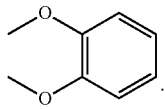

In certain embodiments, the first step in the synthesis of COH29 is the conversion of the starting material compound to a first intermediate compound having the structure:

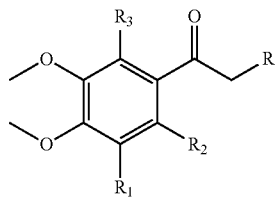

Structure III where R is a substituted or unsubstituted aryl, including for example a phenyl, and $R_1$, $R_2$, and $R_3$ are each independently hydrogen, a substituted or unsubstituted aryl, or a substituted or unsubstituted alkyl. In certain of these embodiments, the first intermediate compound is 1-(3,4-dimethoxyphenyl)-2-phenylethanone, which has the structure:

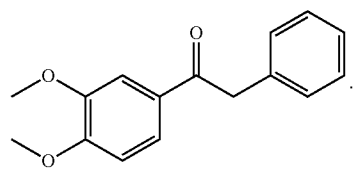 [SMILES: COc1ccc(C(=O)Cc2ccccc2)cc1OC]

In certain embodiments, the starting material compound is converted to the first intermediate compound by adding the starting material compound to a mixture comprising anhydrous $AlCl_3$ in dichloromethane ($CH_2Cl_2$) and a compound having the structure:

or a pharmaceutically acceptable salt, solvate, stereoisomer, or prodrug derivative thereof, wherein:

$R_1$ and $R_2$ are independently selected from the group consisting of hydrogen, alkyl, and aryl groups;

$R_3$ is selected from the group consisting of alkyl groups; and

X is selected from the group consisting of Br, halogen, alkyl and aryl groups.

In certain embodiments, an RR inhibitor as disclosed herein is:

(Structure I)

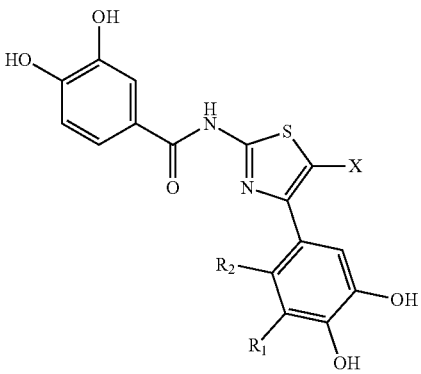

or a pharmaceutically acceptable salt, solvate, stereoisomer, or prodrug derivative thereof, wherein

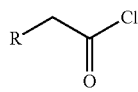

Structure IV where R is a substituted or unsubstituted aryl, including for example a phenyl. In certain embodiments, the compound of Structure IV is phenylacetyl chloride. In certain embodiments, the first intermediate compound is precipitated from the combined organic layers, for example using dichloromethane and/or hexanes. In certain embodiments, the first step of a COH29 synthesis method as provided herein is summarized as follows:

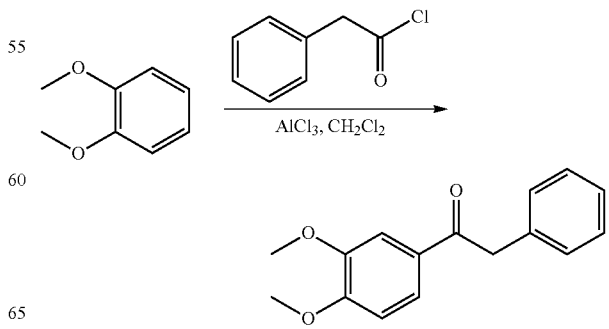

In certain embodiments, the second step in the synthesis of COH29 is the conversion of a first intermediate compound of Structure III to a second intermediate compound having the structure:

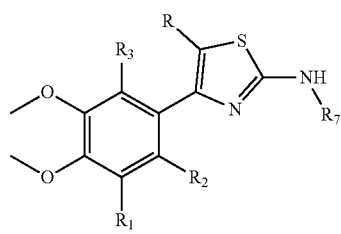

Structure V where R is a substituted or unsubstituted aryl, including for example a phenyl, and $R_1$, $R_2$, $R_3$, and $R_7$ are each independently hydrogen, a substituted or unsubstituted aryl, or a substituted or unsubstituted alkyl. In certain of these embodiments, the second intermediate compound is 4-(3,4-dimethoxyphenyl)-5-phenylthiazol-2-amine which has the structure:

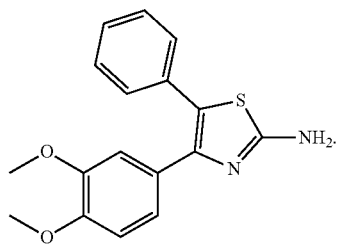 [SMILES: COc1ccc(-c2nc(N)sc2-c2ccccc2)cc1OC]

In certain embodiments, the first intermediate compound is converted to the second intermediate compound by dissolving the first intermediate compound and pyridinium tribromide in dichloromethane, followed by washing and drying. In certain embodiments, the dried reaction mixture is then mixed with thiourea in ethanol. In certain embodiments, the resultant product can be concentrated, washed, and purified by trituration and drying.

In certain embodiments, the second step of a COH29 synthesis method as provided herein is summarized as follows:

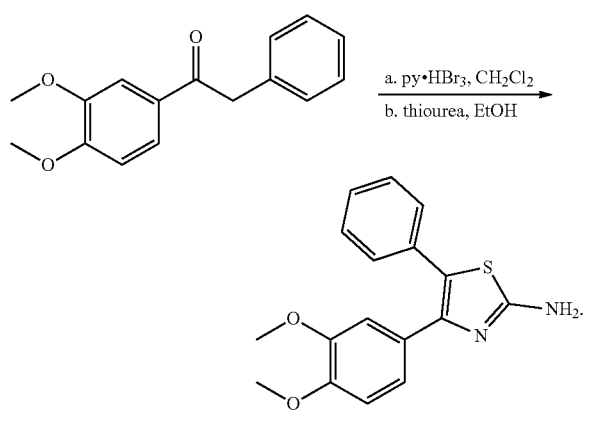

In certain embodiments, the third step in the synthesis of COH29 is the conversion of a second intermediate compound of Structure V to a third intermediate compound having the structure:

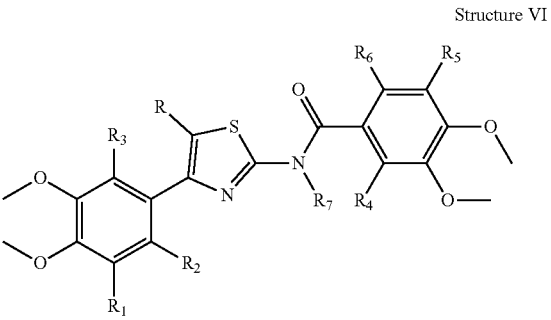

Structure VI where R is a substituted or unsubstituted aryl, including for example a phenyl, and $R_1$, $R_2$, $R_3$, $R_4$, $R_5$, $R_6$, and $R_7$ are each independently hydrogen, a substituted or unsubstituted aryl, or a substituted or unsubstituted alkyl. In certain of these embodiments, the second intermediate compound is N-(4-(3,4-dimethoxyphenyl)-5-phenylthiazol-2-yl)-3,4-dimethoxybenzamide, which has the structure:

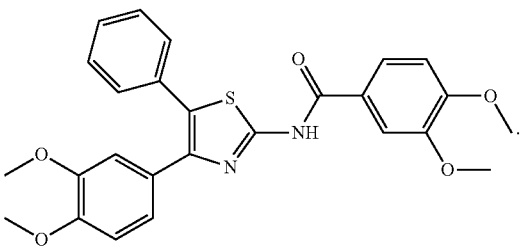

In certain embodiments, a second intermediate compound is converted to a third intermediate compound by adding the second intermediate compound, 4-dimethylamino pyridine, and $Et_3N$ to an acid chloride solution containing 3,4-dimethoxybenzoic acid and dimethylformamide treated with thionyl chloride. In certain embodiments, the reaction may be quenched with $NaHCO_3$. In certain embodiments, the resultant suspension may be extracted with dichloromethane, and in certain of these embodiments the extracted product may be triturated using hexanes.

In certain embodiments, the third step of a COH29 synthesis method as provided herein is summarized as follows:

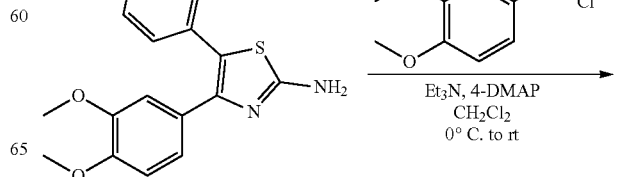

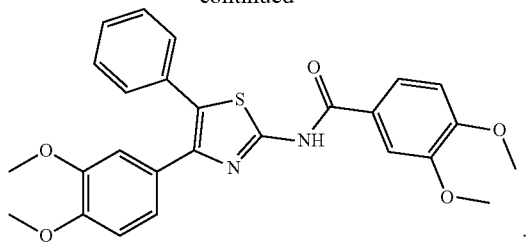

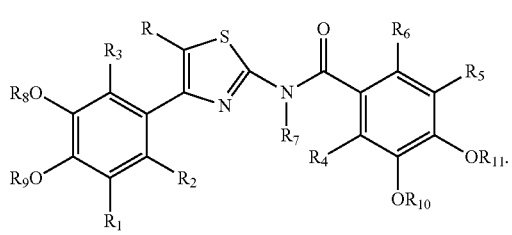

Structure VIA

In certain embodiments, the fourth step in the synthesis of COH29 is the conversion of a third intermediate compound of Structure VI to COH29. In certain of these embodiments, the third intermediate compound is mixed with boron tribromide in toluene, and in certain of these embodiments the reaction is quenched with ethanol, followed by precipitation from water. In certain embodiments, the resultant product undergoes one or more purification steps. In certain of these embodiments, the product is purified using a C-18 silica gel, optionally followed by crystallization.

In certain embodiments, the fourth step of a COH29 synthesis method as provided herein is summarized as follows:

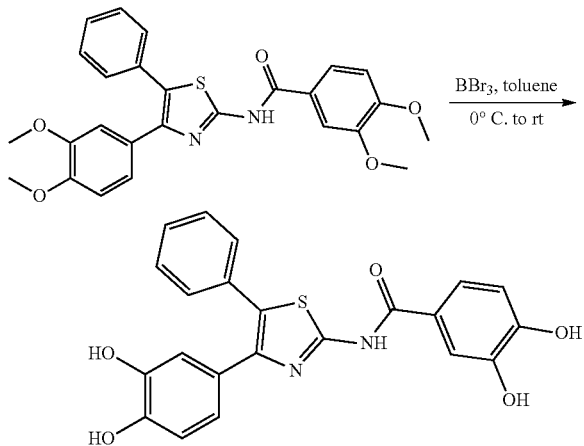

In certain embodiments, synthesis of COH29 results in a final yield of 50% or greater, and in certain of these embodiments the final yield is 60% or greater, 70% or greater, 80% or greater, or 90% or greater.

Figure 26:
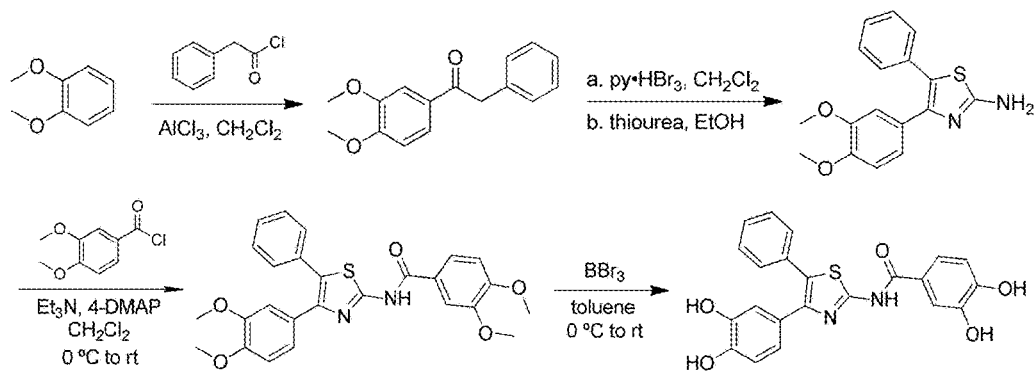
FIG. 26: Synthesis of COH29.

In certain embodiments, methods are provided for the large-scale synthesis of COH29 using the synthetic pathway set forth in FIG. 26.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

In certain embodiments, a compound is provided having the formula:

In Structure VIA, R is substituted or unsubstituted aryl. In embodiments, R is unsubstituted phenyl. $R_1$, $R_2$, $R_3$, $R_4$, $R_5$, $R_6$, and $R_7$ are independently hydrogen, —OH, —NH$_2$, —SH, —CN, —CF$_3$, —NO$_2$, oxo, halogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R_7$ is not —OH, —NH$_2$, —SH, —CN, —CF$_3$, —NO$_2$, oxo or halogen. $R_8$, $R_9$, $R_{10}$ and $R_{11}$ are independently a hydroxyl protecting group. $R_8$ and $R_9$ are optionally joined together to form a substituted or unsubstituted heterocycloalkyl (e.g. 5 membered heterocycloalkyl). $R_{10}$ and $R_{11}$ are optionally joined together to form a substituted or unsubstituted heterocycloalkyl (e.g. 5 membered heterocycloalkyl). $R_1$, $R_2$, $R_3$, $R_4$, $R_5$, $R_6$, and $R_7$ may also independently be hydrogen, substituted or unsubstituted aryl (e.g. phenyl), or a substituted or unsubstituted alkyl (e.g. $C_1$-$C_{10}$ alkyl).

Where $R_1$, $R_2$, $R_3$, $R_4$, $R_5$, $R_6$, or $R_7$ are a substituted alkyl, substituted heteroalkyl, substituted cycloalkyl, substituted heterocycloalkyl, substituted aryl or substituted heteroaryl, the substituent may be a substituent group, as defined above. The substituent may also be a size-limited substituent group, as defined above. The substituent may also be a lower substituent group, as defined above.

Where R is a substituted aryl, the substituent may be a substituent group, as defined above. The substituent may also be a size-limited substituent group, as defined above. The substituent may also be a lower substituent group, as defined above.

In embodiments, $R_8$, $R_9$, $R_{10}$ and $R_{11}$ are independently substituted or unsubstituted alkyl (e.g. $C_1$-$C_{10}$ alkyl), substituted or unsubstituted heteroalkyl (e.g. 2 to 10 membered heteroalkyl), substituted or unsubstituted cycloalkyl (e.g. $C_3$-$C_8$ cycloalkyl), substituted or unsubstituted heterocycloalkyl (e.g. 3 to 6 membered heterocycloalkyl), substituted or unsubstituted aryl (e.g. phenyl), or substituted or unsubstituted heteroaryl (e.g. 5 or 6 membered heteroaryl). In embodiments, $R_8$, $R_9$, $R_{10}$ and $R_{11}$ are substituted or unsubstituted alkyl (e.g. $C_1$-$C_{10}$ alkyl), substituted or unsubstituted heteroalkyl (e.g. 2 to 10 membered heteroalkyl), or substituted or unsubstituted aryl (e.g. phenyl). In embodiments, $R_8$, $R_9$, $R_{10}$ and $R_{11}$ are independently a substituted silyl. A "substituted silyl" as used herein, refers to a substituted heteroalkyl wherein at least one of the heteroatoms is a silicon atom. The silicon atom may be directly attached to the oxygen atom of the hydroxyl that is protected thereby forming a silyl ether. In embodiments, the substituted silyl is substituted with an unsubstituted alkyl (e.g. $C_1$-$C_5$ alkyl), unsubstituted heteroalkyl (e.g. 2 to 5 membered heteroalkyl), unsubstituted cycloalkyl (e.g. $C_3$-$C_6$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl). In embodiments, the substituted silyl is substituted with an unsubstituted alkyl (e.g. $C_1$-$C_5$ alkyl), unsubstituted aryl (e.g. phenyl), or unsubstituted heteroaryl (e.g. 5 or 6 membered heteroaryl). In related embodiments, the silicon atom of the substituted silyl is directly attached to the oxygen atom of the remainder of the compound thereby forming a silyl ether.

Where $R_8$, $R_9$, $R_{10}$ and $R_{11}$ are a substituted alkyl, substituted heteroalkyl (e.g. substituted silyl), substituted cycloalkyl, substituted heterocycloalkyl, substituted aryl or substituted heteroaryl, the substituent may be a substituent group, as defined above. The substituent may also be a size-limited substituent group, as defined above. The substituent may also be a lower substituent group, as defined above.

$R_1$, $R_2$, $R_3$, $R_4$, $R_5$, $R_6$, and $R_7$ may also independently be hydrogen, —OH, —$NH_2$, —SH, —CN, —$CF_3$, —$NO_2$, oxo, halogen, $R_{17}$-substituted or unsubstituted alkyl (e.g. $C_1$-$C_{10}$ alkyl), $R_{17}$-substituted or unsubstituted heteroalkyl (e.g. 2 to 10 membered heteroalkyl), $R_{17}$-substituted or unsubstituted cycloalkyl (e.g. $C_3$-$C_8$ cycloalkyl), $R_{17}$-substituted or unsubstituted heterocycloalkyl (e.g. 3 to 6 membered heterocycloalkyl), $R_{17}$-substituted or unsubstituted aryl (e.g. phenyl), or $R_{17}$-substituted or unsubstituted heteroaryl (e.g. 5 or 6 membered heteroaryl). In embodiments, $R_7$ is not —OH, —$NH_2$, —SH, —CN, —$CF_3$, —$NO_2$, oxo or halogen. $R_8$ and $R_9$ may optionally be joined together to form a $R_{18}$-substituted or unsubstituted heterocycloalkyl (e.g. 5 membered heterocycloalkyl). $R_{10}$ and $R_{11}$ may optionally be joined together to form a $R_{19}$-substituted or unsubstituted heterocycloalkyl (e.g. 5 membered heterocycloalkyl). R may be $R_{19A}$-substituted or unsubstituted aryl. $R_8$, $R_9$, $R_{10}$ and $R_{11}$ may be $R_{19B}$-substituted or unsubstituted alkyl (e.g. $C_1$-$C_{10}$ alkyl), $R_{19B}$-substituted or unsubstituted heteroalkyl (e.g. 2 to 10 membered heteroalkyl), $R_{19B}$-substituted or unsubstituted cycloalkyl (e.g. $C_3$-$C_8$ cycloalkyl), $R_{19B}$-substituted or unsubstituted heterocycloalkyl (e.g. 3 to 6 membered heterocycloalkyl), $R_{19B}$-substituted or unsubstituted aryl (e.g. phenyl), or $R_{19B}$-substituted or unsubstituted heteroaryl (e.g. 5 or 6 membered heteroaryl).

$R_{12}$, $R_{13}$, $R_{14}$, $R_{15}$ and $R_{16}$ may independently be $R_{19C}$-substituted or unsubstituted alkyl (e.g. $C_1$-$C_{10}$ alkyl), $R_{19C}$-substituted or unsubstituted heteroalkyl (e.g. 2 to 10 membered heteroalkyl), $R_{19C}$-substituted or unsubstituted cycloalkyl (e.g. $C_3$-$C_8$ cycloalkyl), $R_{19C}$-substituted or unsubstituted heterocycloalkyl (e.g. 3 to 6 membered heterocycloalkyl), $R_{19C}$-substituted or unsubstituted aryl (e.g. phenyl), or $R_{19C}$-substituted or unsubstituted heteroaryl (e.g. 5 or 6 membered heteroaryl). $R_{12}$, $R_{13}$, $R_{14}$, $R_{15}$ and $R_{16}$ may independently be $R_{19C}$-substituted or unsubstituted alkyl (e.g. $C_1$-$C_{10}$ alkyl), or $R_{19C}$-substituted or unsubstituted aryl (e.g. phenyl).

Each $R_{17}$, $R_{18}$, $R_{19}$, $R_{19A}$, $R_{19B}$ and $R_{19C}$ are independently —OH, —$NH_2$, —SH, —CN, —$CF_3$, —$NO_2$, oxo, halogen, $R_{20}$-substituted or unsubstituted alkyl (e.g. $C_1$-$C_{10}$ alkyl), $R_{20}$-substituted or unsubstituted heteroalkyl (e.g. 2 to 10 membered heteroalkyl), $R_{20}$-substituted or unsubstituted cycloalkyl (e.g. $C_3$-$C_8$ cycloalkyl), $R_{20}$-substituted or unsubstituted heterocycloalkyl (e.g. 3 to 6 membered heterocycloalkyl), $R_{20}$-substituted or unsubstituted aryl (e.g. phenyl), or $R_{20}$-substituted or unsubstituted heteroaryl (e.g. 5 or 6 membered heteroaryl). Each $R_{20}$ is independently —OH, —$NH_2$, —SH, —CN, —$CF_3$, —$NO_2$, oxo, halogen, $R_{21}$-substituted or unsubstituted alkyl (e.g. $C_1$-$C_{10}$ alkyl), $R_{21}$-substituted or unsubstituted heteroalkyl (e.g. 2 to 10 membered heteroalkyl), $R_{21}$-substituted or unsubstituted cycloalkyl (e.g. $C_3$-$C_8$ cycloalkyl), $R_{21}$-substituted or unsubstituted heterocycloalkyl (e.g. 3 to 6 membered heterocycloalkyl), $R_{21}$-substituted or unsubstituted aryl (e.g. phenyl), or $R_{21}$-substituted or unsubstituted heteroaryl (e.g. 5 or 6 membered heteroaryl). Each $R_{21}$ is independently —OH, —$NH_2$, —SH, —CN, —$CF_3$, —$NO_2$, oxo, halogen, unsubstituted alkyl (e.g. $C_1$-$C_{10}$ alkyl), unsubstituted heteroalkyl (e.g. 2 to 10 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl) or unsubstituted heteroaryl (e.g. 5 or 6 membered heteroaryl).

In embodiments, each $R_{17}$, $R_{18}$, $R_{19}$, $R_{19A}$, $R_{19B}$ and $R_{19C}$ are independently —OH, —$NH_2$, —SH, —CN, —$CF_3$, —$NO_2$, oxo, halogen, unsubstituted alkyl (e.g. $C_1$-$C_{10}$ alkyl), unsubstituted heteroalkyl (e.g. 2 to 10 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

In embodiments, $R_1$, $R_2$, $R_3$, $R_4$, $R_5$, $R_6$, and $R_7$ are independently hydrogen, —OH, —$NH_2$, —SH, —CN, —$CF_3$, —$NO_2$, oxo, halogen, unsubstituted alkyl (e.g. $C_1$-$C_{10}$ alkyl), unsubstituted heteroalkyl (e.g. 2 to 10 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl). In embodiments, at least one of $R_1$, $R_2$, $R_3$, $R_4$, $R_5$, $R_6$, and $R_7$ is hydrogen. In embodiments, at least two of $R_1$, $R_2$, $R_3$, $R_4$, $R_5$, $R_6$, and $R_7$ are hydrogen. In embodiments, at least three of $R_1$, $R_2$, $R_3$, $R_4$, $R_5$, $R_6$, and $R_7$ are hydrogen. In embodiments, at least four of $R_1$, $R_2$, $R_3$, $R_4$, $R_5$, $R_6$, and $R_7$ are hydrogen. In embodiments, at least five of $R_1$, $R_2$, $R_3$, $R_4$, $R_5$, $R_6$, and $R_7$ are hydrogen. In embodiments, at least six of $R_1$, $R_2$, $R_3$, $R_4$, $R_5$, $R_6$, and $R_7$ are hydrogen. In embodiments, $R_1$, $R_2$, $R_3$, $R_4$, $R_5$, $R_6$, and $R_7$ are hydrogen.

In embodiments, $R_8$, $R_9$, $R_{10}$ and $R_{11}$ are independently unsubstituted alkyl (e.g. $C_1$-$C_{10}$ alkyl), unsubstituted heteroalkyl (e.g. 2 to 10 membered heteroalkyl), unsubstituted cycloalkyl (e.g. $C_3$-$C_8$ cycloalkyl), unsubstituted heterocycloalkyl (e.g. 3 to 6 membered heterocycloalkyl), unsubstituted aryl (e.g. phenyl), or unsubstituted heteroaryl (e.g. 5 or 6 membered heteroaryl).

In embodiments, $R_8$, $R_9$, $R_{10}$ and $R_{11}$ are independently an activated ethylene protecting group, a benzyl ether protecting group, a silicon-based carbonate protecting group, or a cyclic acetal protecting group. In embodiments, $R_8$, $R_9$, $R_{10}$ and $R_{11}$ are methyl benzyl, p-methoxybenzyl, allyl, trityl, p-methoxyphenyl, tetrahydropyranyl, methoxymethyl, 1-ethoxyethyl, 2-methoxy-2-propy, 2,2,2-trichloroethoxymethyl, 2-methoxyethoxymethyl, 2-trimethylsilylethoxymethyl, methylthiomethyl, trimethylsilyl, triethylsilyl, triisopropylsilyl, triphenylsilyl, t-butyldimethylsilyl, t-butyldiphenylsilyl,

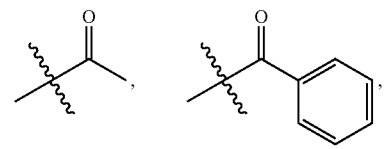

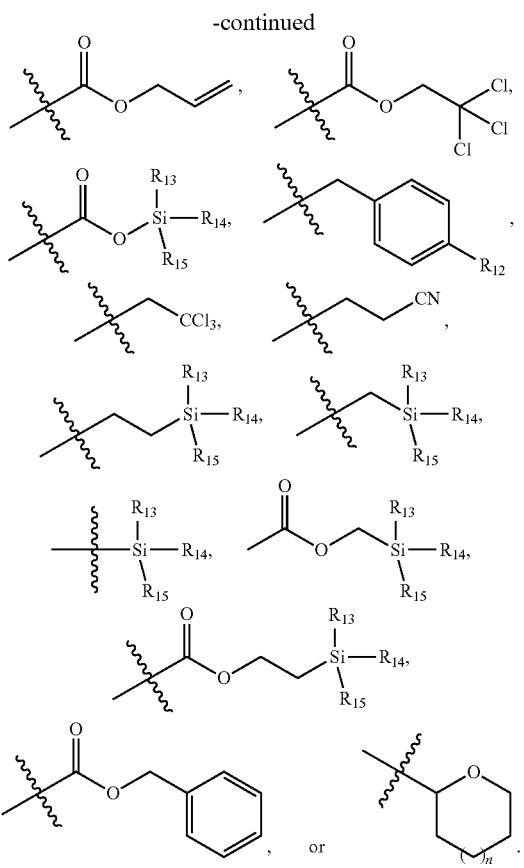

The symbol n is 0 or 1. $R_{12}$ is hydrogen, —OH, —OR$_{16}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R_{12}$ is hydrogen, —OH, —OR$_{16}$ or substituted or unsubstituted alkyl. In embodiments, $R_{12}$ is hydrogen. $R_{16}$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R_{16}$ is substituted or unsubstituted alkyl. $R_{13}$, $R_{14}$ and $R_{15}$ are independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiment, $R_{13}$, $R_{14}$ and $R_{15}$ are independently substituted or unsubstituted alkyl or substituted or unsubstituted aryl.

Where $R_{12}$, $R_{13}$, $R_{14}$ $R_{15}$ and $R_{16}$ is a substituted alkyl, substituted heteroalkyl, substituted cycloalkyl, substituted heterocycloalkyl, substituted aryl or substituted heteroaryl, the substituent may be a substituent group, as defined above. The substituent may also be a size-limited substituent group, as defined above. The substituent may also be a lower substituent group, as defined above.

In embodiments, $R_{12}$ is hydrogen, methyl or —OCH$_3$. $R_{13}$, $R_{14}$ and $R_{15}$ may be unsubstituted $C_1$-$C_5$ alkyl or unsubstituted phenyl. In embodiments, $R_{13}$, $R_{14}$ and $R_{15}$ may be unsubstituted $C_1$-$C_5$ alkyl.

In embodiments, R is unsubstituted aryl (e.g. phenyl). $R_1$, $R_2$, $R_3$, $R_4$, $R_5$, $R_6$, and $R_7$ may independently be hydrogen, unsubstituted aryl (e.g. phenyl), or unsubstituted alkyl (e.g. $C_1$-$C_5$ alkyl).

In embodiments, $R_8$ and $R_9$ are optionally joined together to form an acetal protecting group and $R_{10}$ and $R_{11}$ are optionally joined together to form an acetal protecting group. An "acetal protecting group" is used according to its common meaning in the art of chemical synthesis, in which an acetal group is frequently used to protect catechol hydroxyl moieties. An acetal protecting group may have the formula:

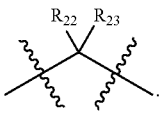

Structure VIC

In Structure VIC, $R_{22}$ and $R_{23}$ are independently hydrogen, substituted or unsubstituted alkyl (e.g. $C_1$ to $C_5$ alkyl, such as methyl) or substituted or unsubstituted aryl (e.g. phenyl). The symbol ～ represents the point of attachment to the catechol oxygen atoms (i.e. oxygen atoms attached to $R_8$, $R_9$ and $R_{10}$ and $R_{11}$, respectively). In embodiments, $R_{22}$ and $R_{23}$ are independently hydrogen, unsubstituted alkyl (e.g. $C_1$ to $C_5$ alkyl, such as methyl) or unsubstituted aryl (e.g. phenyl). In some embodiments, $R_{22}$ and $R_{23}$ are hydrogen. In embodiments, $R_{22}$ and $R_{23}$ are unsubstituted alkyl (e.g. $C_1$ to $C_5$ alkyl). In embodiments, $R_{22}$ and $R_{23}$ are methyl. In some embodiments, $R_{22}$ and $R_{23}$ are unsubstituted aryl (e.g. phenyl). In embodiments, the acetal protecting group is a diphenyl methylene acetal.

In embodiments, the compound of Structure VIA has the formula:

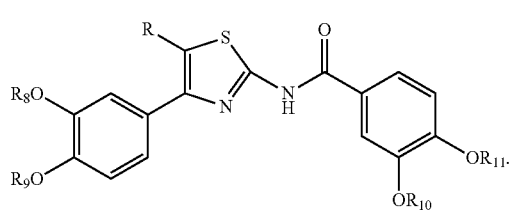

Structure VIB

In Structure VIB, R, $R_8$, $R_9$, $R_{10}$ and $R_{11}$ are as defined above, including all embodiments thereof. In embodiments of the compound of Structure VIA or VIB, R is unsubstituted aryl. In embodiments of Structure VI or VIB, R is unsubstituted phenyl.

In embodiments, a composition is provided including the compound of Structure VIA or embodiments thereof, or Structure VIB or embodiments thereof, and an organic solvent (e.g. a non-polar solvent of a polar aprotic solvent). In embodiments, the organic solvent is a non-polar solvent (e.g. toluene or 1,4-dioxane). In embodiments, the organic solvent is dioxane. In embodiments, the organic solvent is a polar aprotic solvent (e.g. acetone, dimethylformamide, acetonitrile of dimethyl sulfoxide). In embodiments, the organic solvent is dimethyl formamide.

In embodiments, a composition is provided including the compound of Structure VIA or embodiments thereof, or Structure VIB or embodiments thereof and a hydroxyl deprotecting agent. The hydroxyl deprotecting agent is a chemical agent useful in removing a hydroxyl protecting group as described herein. Useful chemical agents are selected as hydroxyl deprotecting agents to minimize degradation of the compound of Structure VIA and embodiments thereof, Structure VIB and embodiments thereof and Structure VID and embodiments thereof. In embodiments, the deprotecting agent is a reducing agent, an acidic agent or a basic agent. In embodiments, the deprotecting agent is boron tribromide, an aryl methyl ether, tetrabutylammonium fluoride, a reducing agent (e.g. a palladium reducing agent such as hydrogen/Pd/C), a metal acid agent (e.g. a Zn/acid such as Zn/acetic acid or Zn/HCl) or ammonia.

In certain embodiments, a method is provided for synthesizing a compound having the structure:

Structure VID

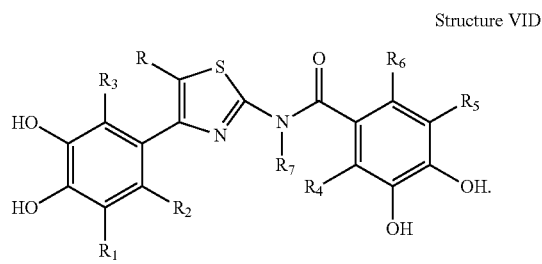

The method includes contacting a hydroxyl deprotecting agent (as described above) with a compound having the formula:

Structure VIA

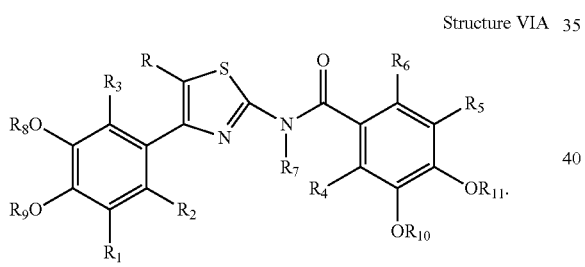

In Structure VIA and Structure VID, R, $R_1$, $R_2$, $R_3$, $R_4$, $R_5$, $R_6$, $R_7$, $R_8$, $R_9$, $R_{10}$ and $R_{11}$ are as defined above, including all embodiments. In embodiments, $R_1$, $R_2$, $R_3$, $R_4$, $R_5$, $R_6$, and $R_7$ are independently hydrogen, substituted or unsubstituted aryl, or a substituted or unsubstituted alkyl. $R_8$, $R_9$, $R_{10}$ and $R_{11}$ may independently be a hydroxyl protecting group. $R_8$ and $R_9$ are optionally joined together to form a substituted or unsubstituted heterocycloalkyl. $R_{10}$ and $R_{11}$ are optionally joined together to form a substituted or unsubstituted heterocycloalkyl.

EXAMPLES

Example 1: Confirmation of RRM2 as a Target for Anti-Cancer Therapy

Figure 1B:
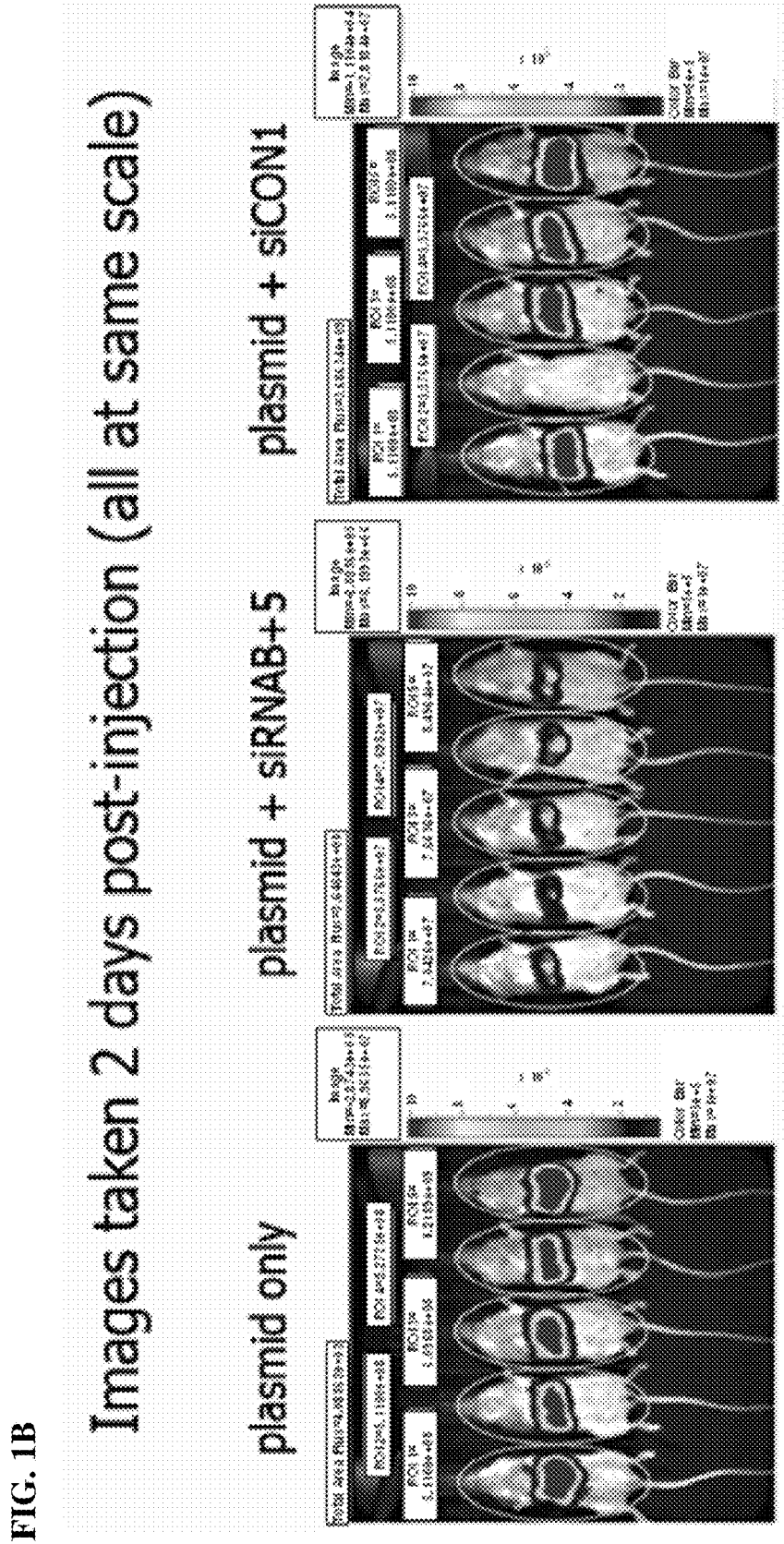

An RRM2-luciferase fusion construct ("pR2Luc") was administered alone or in combination with an RRM2 siRNA ("siR2B+5") by hydrodynamic tail vein injection (HPTV) [plasmid 0.25 mg/kg, siRNA 1.25 mg/kg] to female BALB/c mice implanted with human HepG2 liver cancer cells. In vivo bioluminescence imaging revealed potent down-regulation within mouse liver cancer cells over multiple weeks (FIGS. 1A-1B). Mice receiving RRM2 in combination with RRM2 siRNA exhibited a significant decrease in tumor growth versus mice receiving RRM2 alone or in combination with control siRNA ("siCONTROL"). These results suggest that RRM2 plays critical role in cancer growth and validates it as a therapeutic target.

Figure 2A:
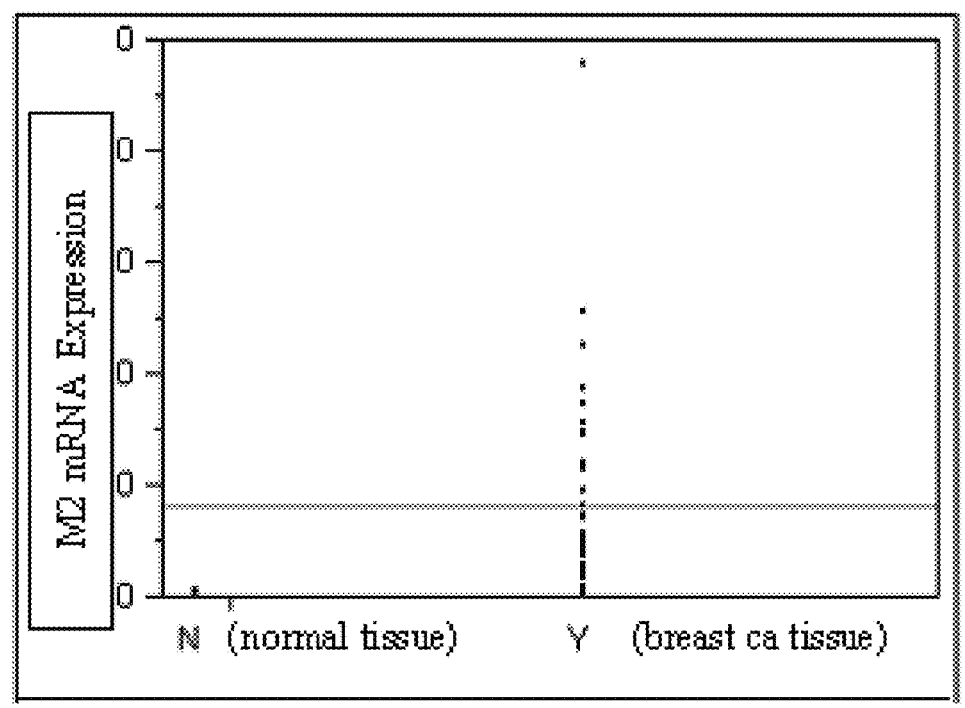
FIGS. 2A-2B: RRM2 overexpression in cancer tissues and cell lines in comparison to normal tissue.
Figure 2B:
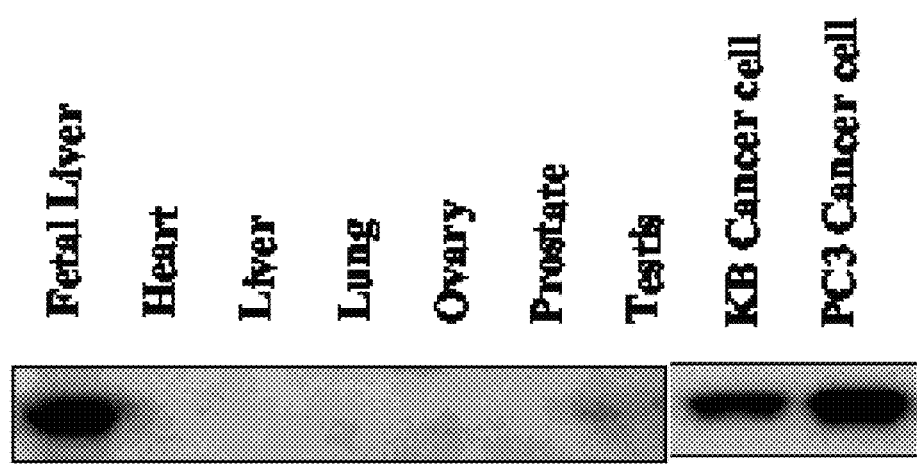

RRM2 mRNA expression levels were measured by RT-PCR in 35 human fresh frozen breast cancer biopsies and corresponding normal tissue samples. Optimal PCR primer and probe concentrations of RRM2 and (3-actin housekeeping gene were determined to reach maximum efficiency during the amplification. The PCR reaction was performed in a 20 μl final volume, adding 1 μL cDNA from each sample using TAQMAN® PCR mix (Applied Biosystems, Foster City, Calif.). A significant increase in RRM2 expression was observed in breast cancer tissue versus corresponding normal tissue ($p<0.05$) (FIG. 2A). A Western blot revealed that normal human tissues other than fetal liver and testis express low levels of RRM2, whereas cancer cells express significantly higher levels of RRM2 (FIG. 2B).

Figure 3A:
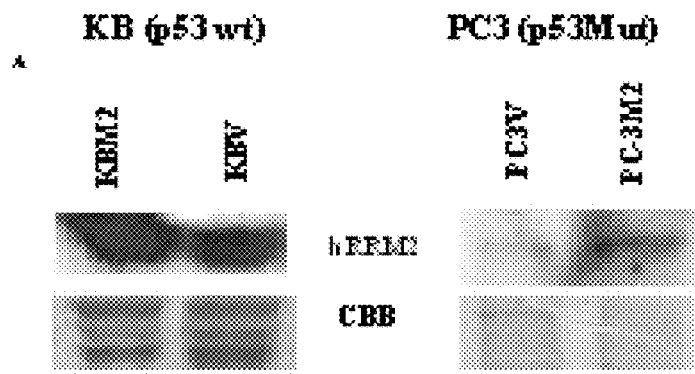
Figure 3B:
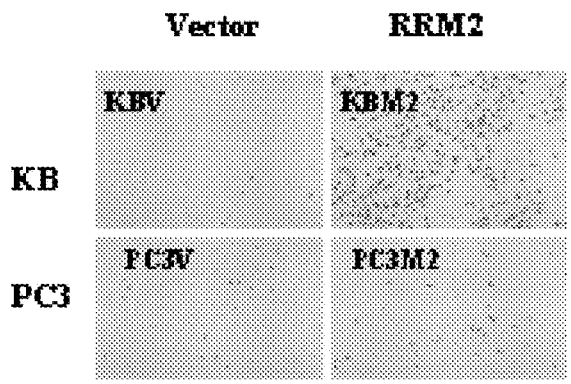

Human oropharyngeal cancer KB (wild-type p53) and human prostate cancer PC3 (truncated p53) cells were transfected with sense RRM2 (KBM2 and PC3M2, respectively) and control vector, and the resulting overexpression of RRM2 was confirmed by Western blot analysis. Transfectants were applied to the upper layer of MATRIGEL® in a Borden chamber. After 72 hours, cells that invaded to the lower layer were fixed with alcohol, stained with methylene blue, and counted and examined. RRM2 transfected cells exhibited increased invasive potential in comparison to non-transfected cells (FIGS. 3A-3C).

Example 2: Identification of Novel RR Inhibitors

Figure 4:
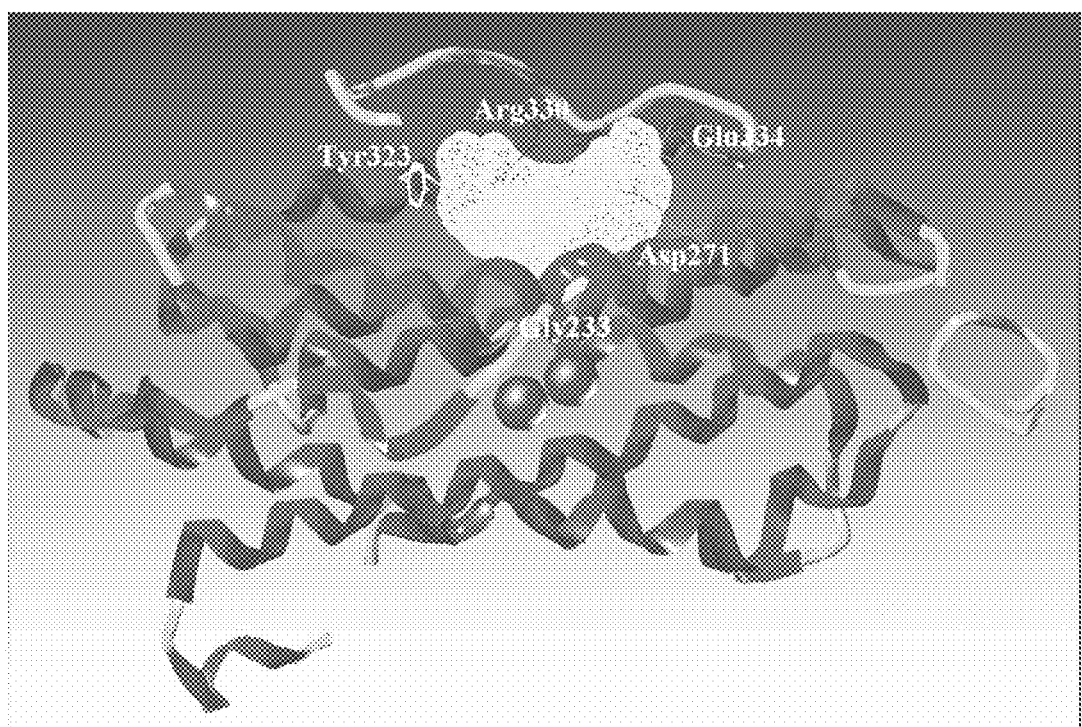
FIG. 4: Prediction of V-shaped ligand binding pocket on RRM2. Iron clusters are shown in red.

A diverse compound library from NCI Developmental Therapeutics Program (DTP) was subjected to a virtual screening process to identify potential RR inhibitors. The DTP library contains 2,000 different compounds. A novel ligand binding pocket on human RRM2 identified from the X-ray crystal structure (PDB 2UW2) was selected to identify potential inhibitor compounds that were in close proximity to the RRM1/RRM2 interface but distant from the dityrosyl-diiron center in order to avoid iron chelating side effects. This ligand binding pocket, which consists of 32 amino acid residues conserved among human and mouse RRM2 protein families, is in close proximity to the RRM1/RRM2 interface. The structure of the ligand binding pocket is set forth in FIG. 4. The pocket consists of helices α7, α8, and α10 at the C-terminal domain. The narrow interior end of the V-shaped pocket is lined up with hydrophobic residues near the back of dityrosyl diiron cluster center. Polar residues such as D271, R330, and E334 that are located near the open-end of the pocket may potentially interact with the flexible C-terminus. The pocket is lined mostly with interior hydrophobic residues with charged residues exposed to the surface.

Compounds that docked into the ligand binding pocket were identified using the TRIPOS FlexX docking tool and ranked using an embedded consensus docking score. The top 80 RR inhibitor candidates that exhibited a binding affinity equal to or greater than that of 3-AP in the virtual screen were subjected to an in vitro screen using a known semi-high throughput holoenzyme-based assay for determining the potency and subunit-selectivity of small molecule inhibitors (Shao 2005). The assay utilized recombinant RRM1/RRM2 or RRM1/RRM2 complex and measured [$^3$H]CDP reduction activity (i.e., CDP to dCDP) by HPLC. Ten compounds exhibited the ability to inhibit native RRM1/RRM2 activity by greater than 50% in vitro, and four of these compounds inhibited enzyme activity by 80% or more. Three of the four compounds exhibiting ≥80% inhibition shared a similar structural scaffold (NCI-3, NSC #659390, and NSC #45382), and also showed better solubility and lower toxicity than the other tested compounds. NCI-3 (dihydroxyphenylthiazole, DHPT) has the following structure:

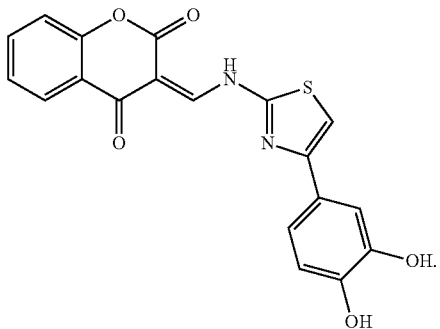 [SMILES: O=C1Oc2ccccc2C(=O)/C1=C/Nc1nc(-c2ccc(O)c(O)c2)cs1]

Figure 5:
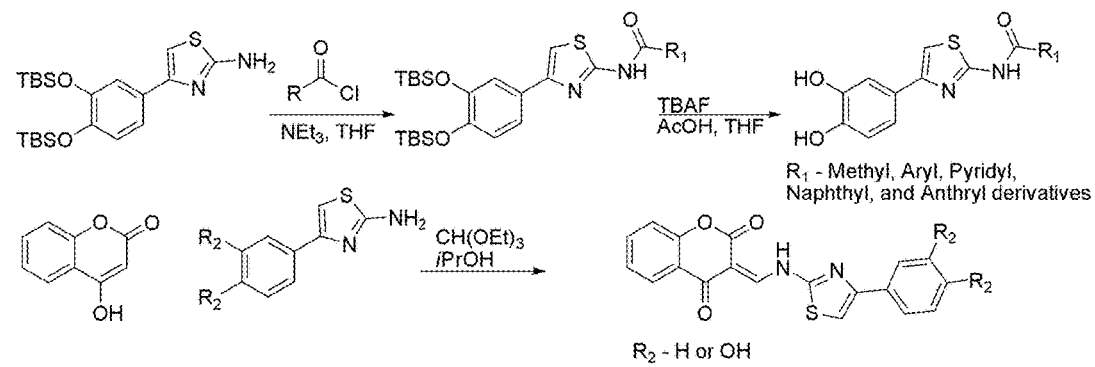
FIG. 5: Synthesis strategy for NCI-3 analogs

A series of NCI-3 analogs were synthesized using the strategy set forth in FIG. 5. An additional 24 NCI-3 analogs were developed by attaching a variety of R groups to the aminothiazole group. Compounds generated in this manner included COH1, COH2, COH4, COH20 and COH29.

Example 3: Characterization of Novel NCI-3 Analogs

Figure 6:
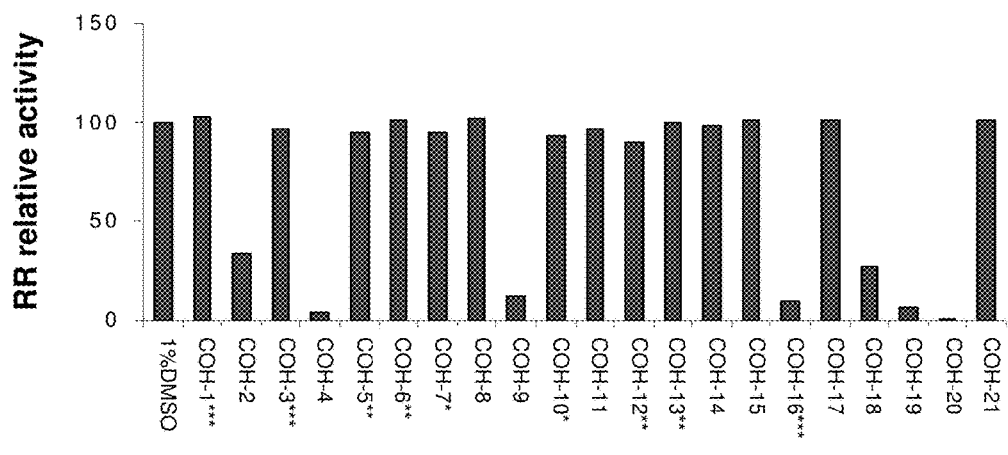
FIG. 6: Inhibition of RR activity in vitro by HU, 3-AP, NCI-3, COH4, and COH20.

The ability of NCI-3 and the NCI-3 analogs synthesized in Example 2 to inhibit RR activity was tested using the in vitro holoenzyme assay described above. COH4 exhibited significant RR inhibition. COH20 was even more effective, causing 90.2% inhibition of the recombinant RRM1/RRM2 complex in vitro (FIG. 6). IC50 results for various compounds are set forth in Table 1.

TABLE 1

| Compound | IC50 ± S.D. (μM) |
|---|---|
| HU | 148.0 ± 7.34 |
| 3-AP | 1.2 ± 0.13 |
| NCI-3 | 19.1 ± 0.43 |
| COH4 | 15.3 ± 1.8 |
| COH20 | 9.3 ± 2.3 |

In striking contrast to 3-AP, inhibition of RR by COH20 was virtually unaffected by the addition of iron (Table 2).

TABLE 2

| | IC50 ± S.D. (μM) RRM1/RRM2 |
|---|---|
| COH20 alone | 9.31 ± 2.3 |
| COH20-Fe complex | 9.12 ± 1.9 |
| COH20-Fe complex with added Fe | 10.41 ± 2.1 |

Site-directed mutagenesis, Biacore analysis, and NMR Saturation Transfer Difference (STD) analysis were carried out to validate the binding pocket and ligand/protein interaction between COH20 and RRM2. RRM2 point mutants were generated by mutating certain key residues in the binding pocket. These residues included Y323, D271, R330, and E334, each of which are charged and reside on the surface of the binding pocket, and G233, which sits deep in the pocket. Attenuation of inhibition in these mutants confirmed involvement of the mutated residues in ligand binding and validated the binding pocket. Interestingly, the only mutation that did not attenuate inhibition was G233V. This suggests the presence of a hydrophobic pocket that is stabilized by introduction of a valine side chain.

Figure 7:
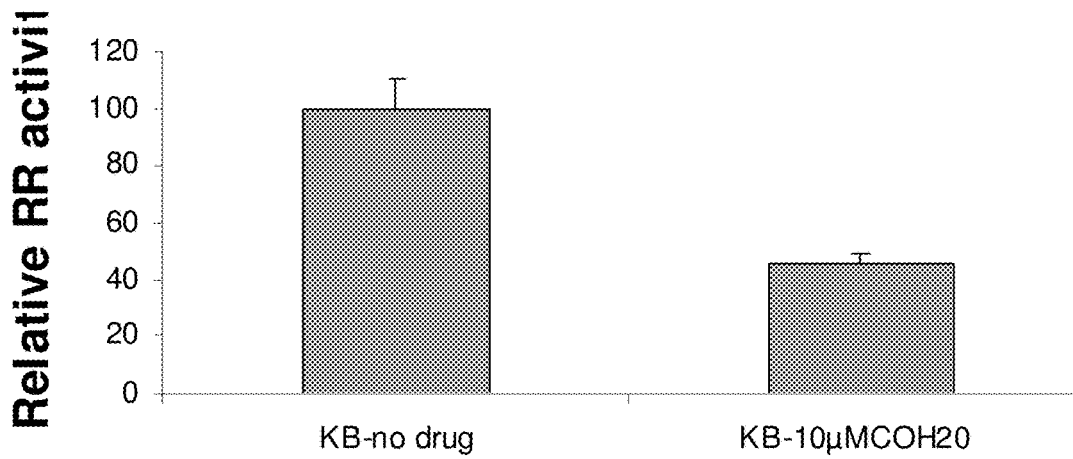
FIG. 7: Inhibition of intracellular RR activity by COH20.
Figure 8:
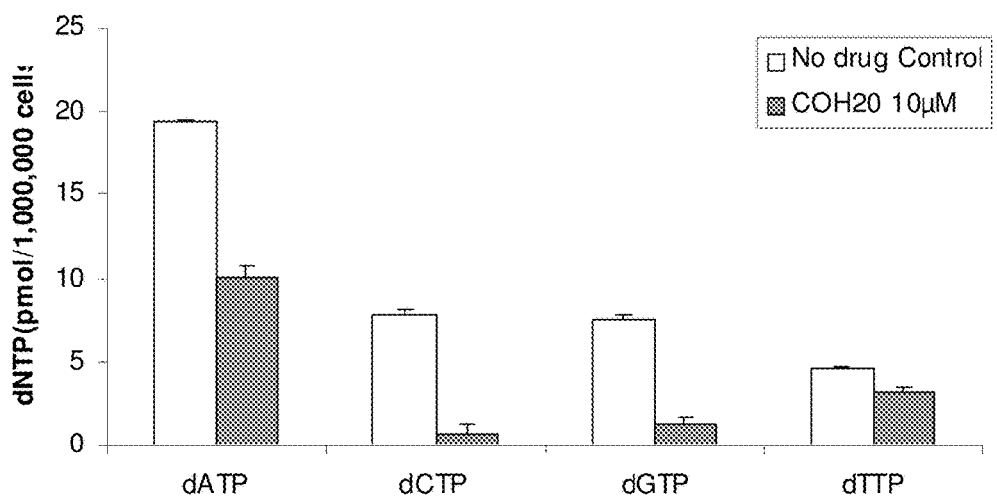
FIG. 8: Inhibition of dNTP pools by COH20 in KB cells.

To confirm that the ability of COH20 to inhibit RR activity was not specific to recombinant RR, an assay was performed testing the effect of COH20 on intracellular RR. KB cells treated with 10 μM COH20 were lysed, and protein was extracted in a high salt buffer and passed through a G25 SEPHADEX® column to remove small molecules such as dNTP. The eluate was mixed with [$^3$H]CDP in reaction buffer to monitor RR activity. Treatment with COH20 decreased intracellular RR activity by approximately 50% (FIG. 7). Treatment with COH20 had no effect on RRM2 protein levels as measured by Western blot, indicating that the effect of COH20 on RR activity is not due to a decrease in RRM2 expression.

dNTP pools from KB cells were measured by polymerase template assay following treatment with 10 μM COH20. Pre- and post-treatment cell pellets were mixed with 100 μl of 15% trichloroacetic acid, incubated on ice for ten minutes, and centrifuged at high speed for five minutes. Supernatants were collected and extracted with two 50 μl aliquots of Freon/trioctylamine (55%/45%) to neutralize the trichloroacetic acid. After each addition, the samples were centrifuged at high speed and supernatant was collected. Two 5 μl aliquots (one for each duplicate) of each sample were used to check dATP, dCTP, dGTP, and dTTP concentrations. The reaction mixture in each tube contained 50 mM Tris-HCL pH 7.5, 10 mM MgCl, 5 mM DTT, 0.25 mM template/primer, 1.25 μM $^3$H-dATP (for dCTP assay) or $^3$H-dTTP (for dATP assay), and 0.3 units of SEQUENASE™ (2.0) in a total volume of 50 μL. DNA synthesis was allowed to proceed for 20 minutes at room temperature. After incubation, 40 μl of each reaction mixture was spotted onto a WHATMAN® DE81 ion exchange paper (2.4 cm diameter). The papers were dried for 30-60 minutes at room temperature, washed with 5% $Na_2HPO_4$ (3×10 minutes), and rinsed once with distilled water and once more with 95% ethanol. Each paper was dried and deposited in a small vial, and 5 ml of scintillation fluid was added to each vial. Tritium-labeled dNTPs were counted using liquid scintillation counter and compared to standards prepared at 0.25, 0.5, 0.75, and 1.0 pmol/μL of dNTPs. For comparison, duplicate sets of reactions were carried out with freshly added inhibitors. COH20 was found to decrease dATP, dCTP, dGTP, and dTTP pools in KB cells, indicating that inhibition of RR results in a concomitant decreased in dNTP production (FIG. 8). Similar experiments will be performed using other cell lines.

Figure 9:
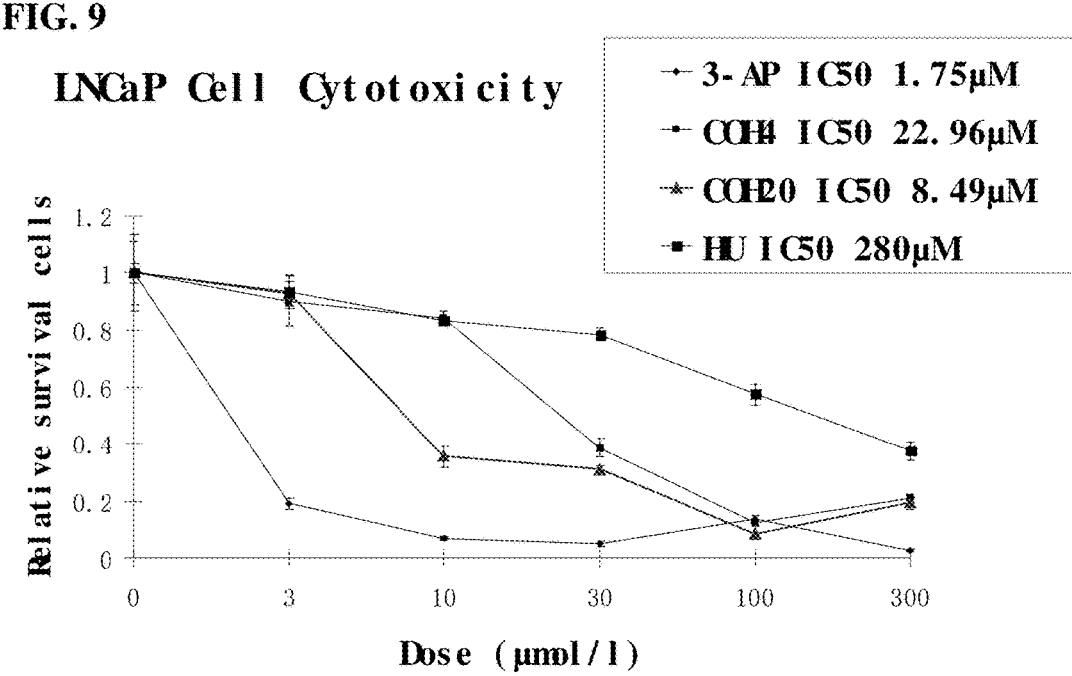
FIG. 9: Cytotoxicity of 3-AP, HU, COH4, and COH20 in human prostate LNCaP cancer cells in vitro.
Figure 10:
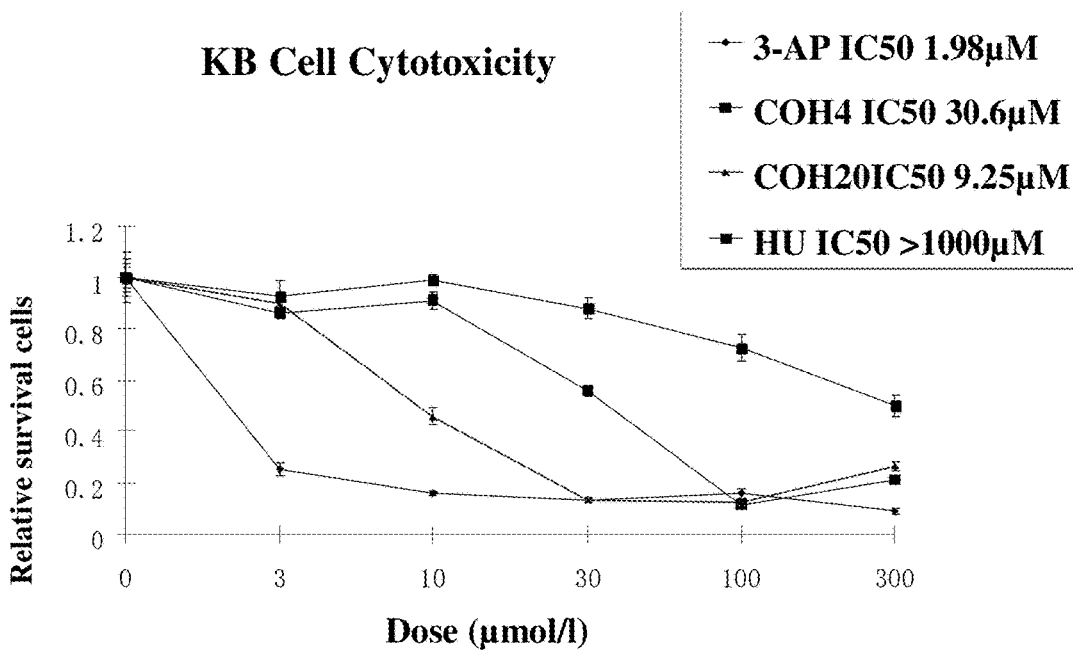
FIG. 10: Cytotoxicity of 3-AP, HU, COH4, and COH20 in human KB cancer cells in vitro.
Figure 11:
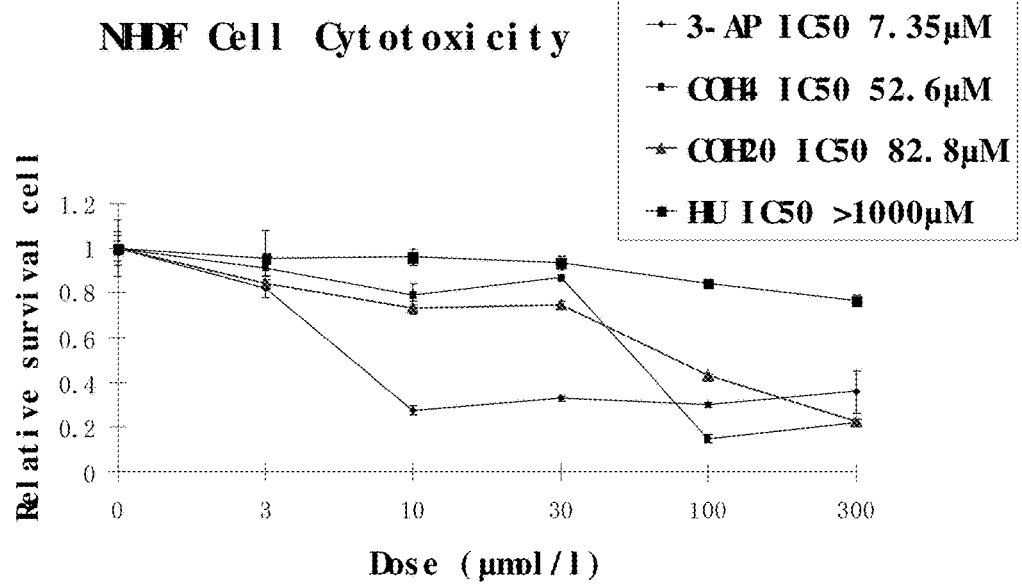
FIG. 11: Cytotoxicity of 3-AP, HU, COH4, and COH20 in normal human fibroblast (NHDF) cells in vitro.

The in vitro cytotoxicity of COH4 and COH20 towards human leukemia REH and MOLT-4 cells, human prostate cancer LNCaP cells, human oropharyngeal cancer KB cells, and normal fibroblast NHDF cells was evaluated using an MTT assay. 5,000 cells were seeded on six-well plates for 72 hours with various concentrations of drug. COH20 was cytotoxic to the cancer cell lines at less than 10 μM, while causing less cytotoxicity to normal cells than 3-AP. The results are summarized in Table 3. Results for LNCaP, KB, and NHDF are set forth in FIGS. 9-11. Based on the broad range of cancer cell types against which COH20 exhibits cytotoxicity, COH20 is expected to be cytotoxic to a variety of additional cancer cell types, including colon cancer, breast cancer, lung cancer, melanoma, leukemia, and lymphoma cells.

TABLE 3

| Cell line | IC50 (μM) | | | |
|---|---|---|---|---|
| | COH20 | COH4 | 3-AP | HU |
| REH | 2.54 | 20.6 | 1.42 | 32.8 |
| MOLT-4 | 5.26 | 11.85 | 1.21 | 165 |
| LNCaP | 8.49 | 22.96 | 1.75 | 280 |
| KB | 9.25 | 30.6 | 1.98 | 300 |
| NHDF | 82.8 | 52.6 | 7.35 | >1000 |

Figure 12:
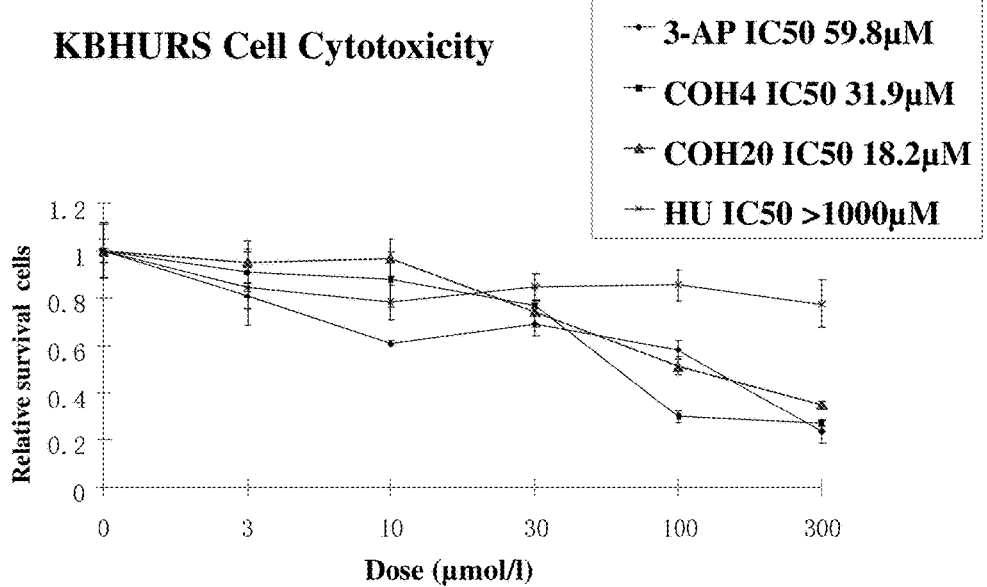
FIG. 12: Cytotoxicity of 3-AP, HU, COH4, and COH20 in human KBHUR cancer cells in vitro.
Figure 13:
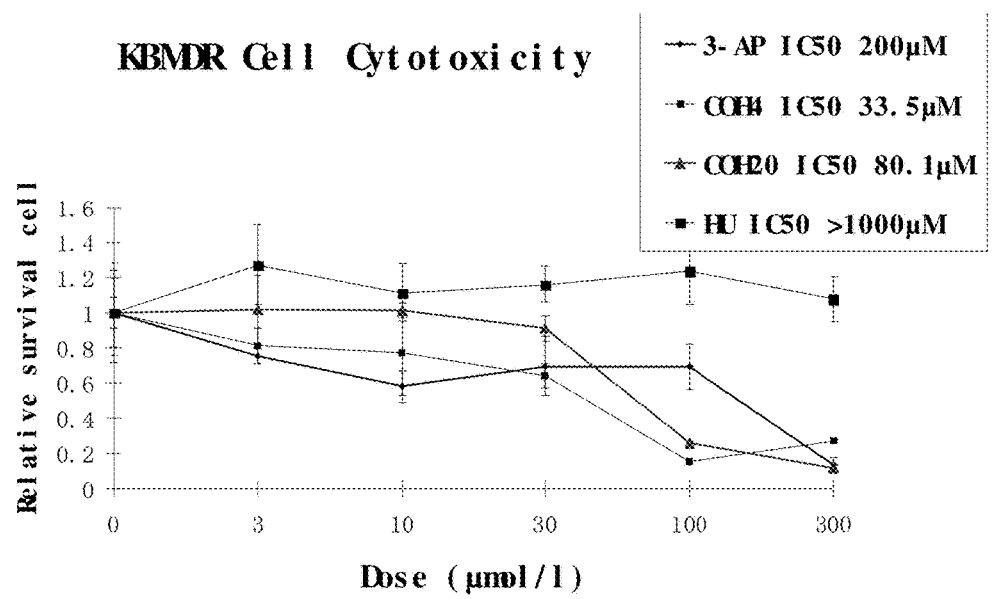
FIG. 13: Cytotoxicity of 3-AP, HU, COH4, and COH20 in human KBMDR (multidrug resistant) cells in vitro.
Figure 14:
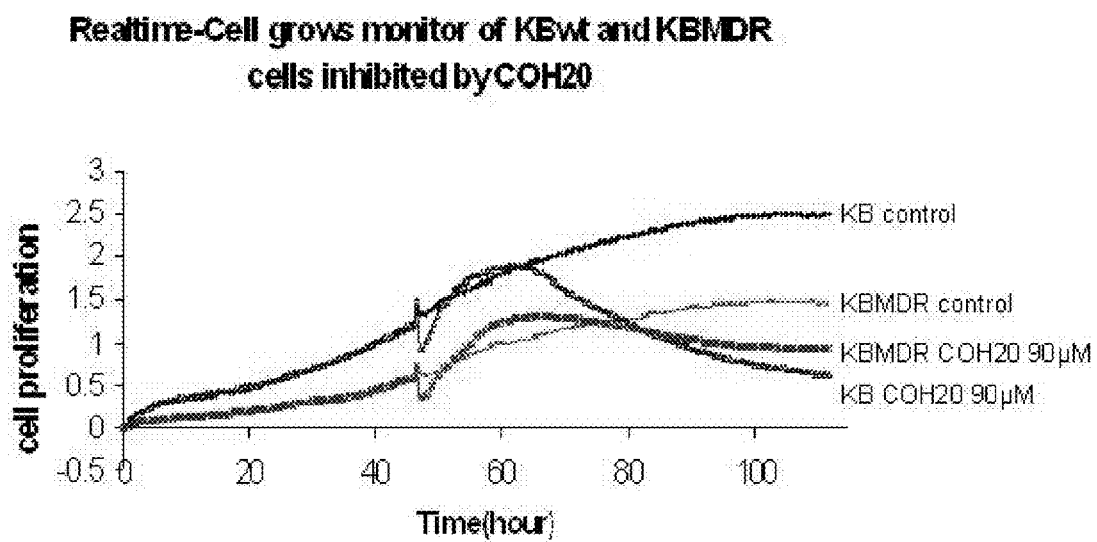
FIG. 14: Inhibition of human KB and KBMDR cell proliferation by COH20.
Figure 15A:
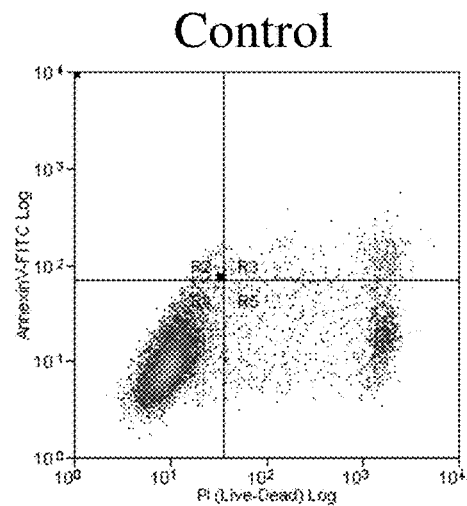
FIGS. 15A-15H: Flow cytometry of KB cells following treatment with 3-AP or COH20 at indicated concentrations.
Figure 15B:
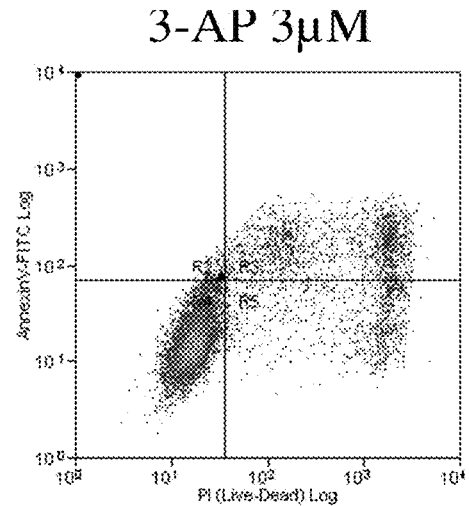
Figure 15C:
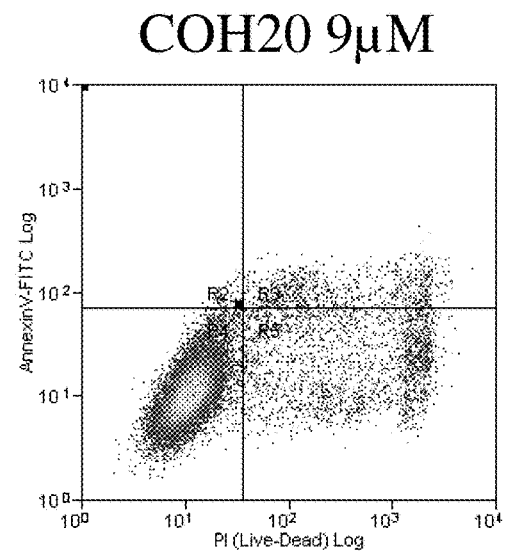
Figure 15D:
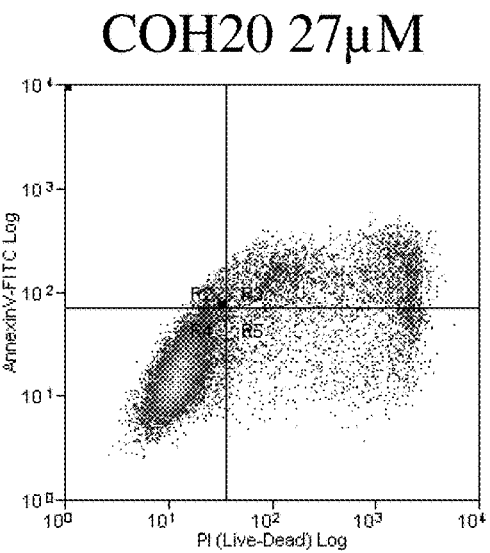
Figure 15E:
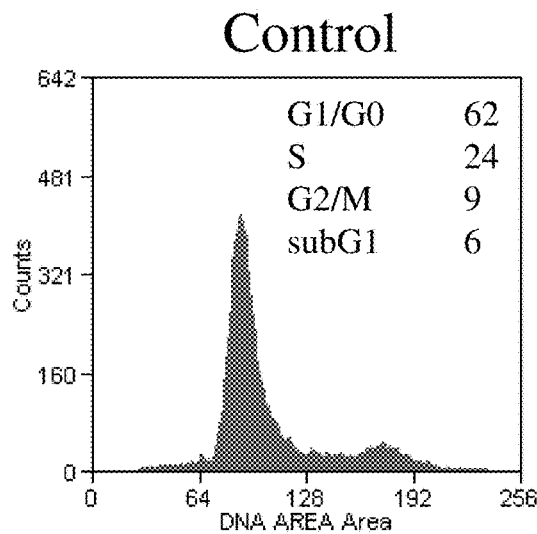
Figure 15F:
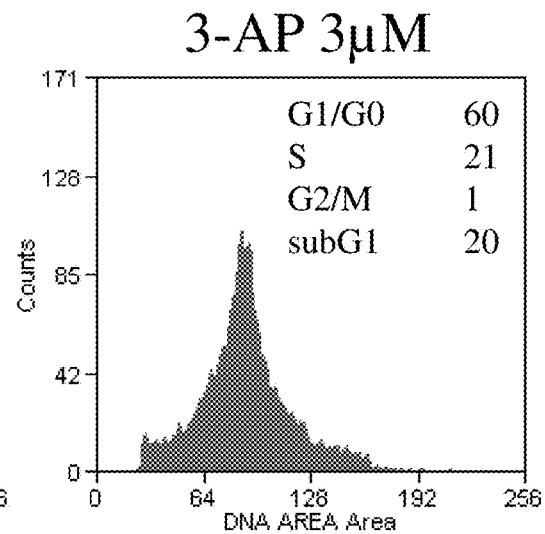
Figure 15G:
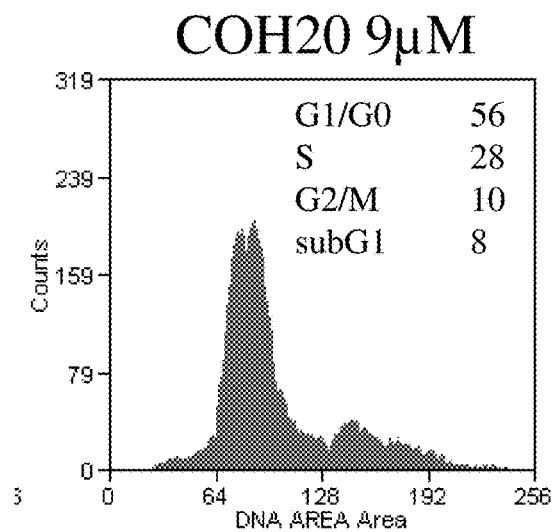
Figure 15H:
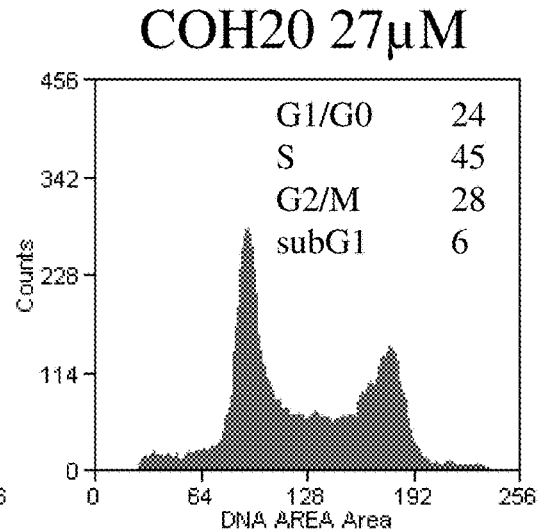

In vitro cytotoxicity assays were repeated using KBHURs, an HU-resistant clone derived from KB cells that overexpresses RRM2. COH20 was cytotoxic to KBHURs at significantly lower concentrations than the other RR inhibitors tested, confirming that COH20 is capable of overcoming HU resistance (FIG. 12). In addition, COH20 was found to be cytotoxic to KBMDR, a KB clone that overexpresses the MDR pump on the cell membrane, at lower concentrations than 3-AP or HU (FIG. 13). A real-time proliferation assay confirmed that COH20 also inhibits cell proliferation in KBMDR cells (FIG. 14). Similar experiments will be repeated using the gemcitabine resistant cell line KBGem, which also overexpresses RRM2. Based on the results with other cell lines, it is expected that COH20 will also exhibit cytotoxicity and growth inhibition towards KBGem.

The in vitro cytotoxicity of COH29 towards a panel of human cancer cell lines was tested using the MTT assay described above. COH29 significantly inhibited growth across a broad range of cancer cell types, with an $IC_{50}$ of less than about 10 μM in all cell types tested except for colon cancer HT29, melanoma UACC-257, ovarian cancer NCI/ADR-RES, and renal cancer CAKI-1 (FIGS. 20-24). Representative results are summarized in Table 4.

TABLE 4

| Cell line | IC50 |
|---|---|
| Leukemia CCRF-CEM | 2.8 μM |
| Leukemia MOLT-4 | 2.5 μM |
| Leukemia SUP B15 | 5.0 μM |
| Ovarian Cancer OV 90 | 2.6 μM |

Flow cytometry and annexin staining were performed on KB cells treated with COH20 at 9 or 27 μM or 3-AP at 3 μM for 24 hours. These results showed that COH20 treatment arrests cells in S-phase in a dose-dependent manner (FIG. 15A-15D). After treatment with COH20 for 72 hours, annexin staining showed significant cell death, indicating apoptosis (FIGS. 15E-15H). COH20 induced apoptosis with approximately the same potency as 3-AP.

Figure 16:
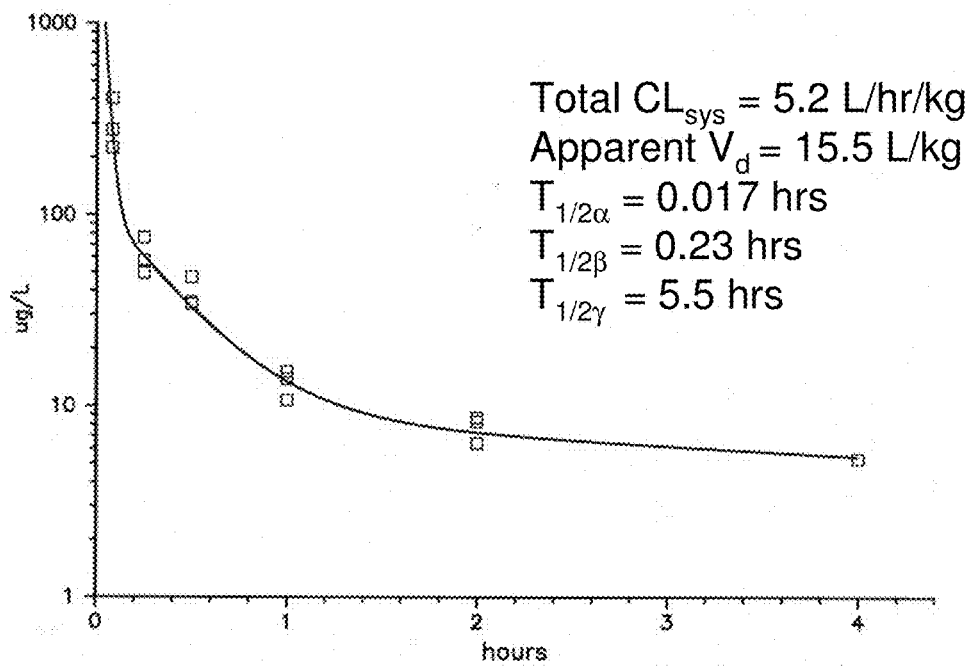
FIG. 16: Single-dose pharmacokinetics of COH20 in rats.

COH20 was injected into three male rats at 1 mg/kg for single-dose pharmacokinetic evaluation. Elimination of COH20 from plasma was found to be tri-exponential, with a rapid initial decline phase (possible tissue distribution or liver uptake) followed by an intermediate phase (combined distribution and elimination) and a slower terminal phase (elimination) (FIG. 16). The terminal half-life ($T_{1/2}$) was approximately 5.5 hours. More detailed pharmacokinetic studies will be performed with various dosages of COH20 to establish parameters such as clearance, bioavailability, and tissue/plasma partition coefficients.

Figure 25:
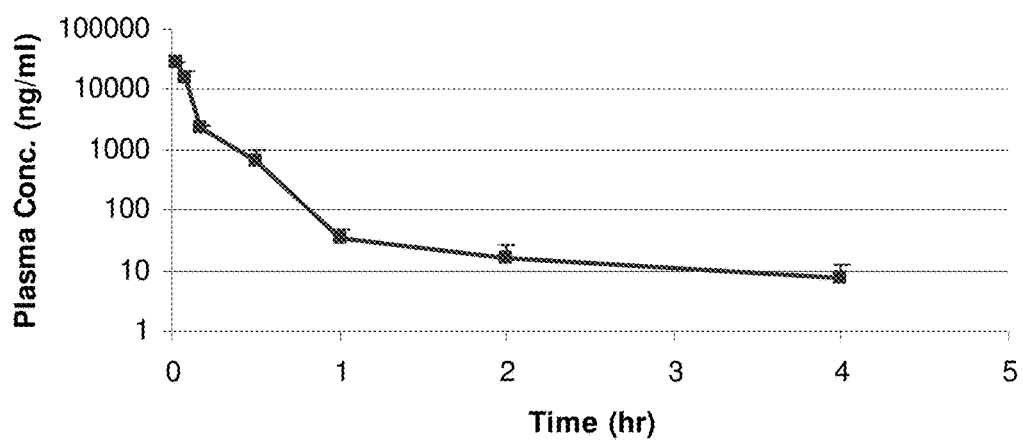
FIG. 25: Pharmacokinetic of COH29 in rats.

Pharmacokinetic evaluation was performed on COH29 using the same techniques, with COH29 administered at a dosage of 25 mg/kg. Results from triplicate analysis are summarized in Table 5. Area under the curve (AUC) calculations showed COH29 acting in a dose-dependent manner when administered by i.v. bolus (FIG. 25).

TABLE 5

| | $C_{max}$ (ng/ml) | $T_{max}$ (hr) | AUC (ng*h/ml) | CL (ml/(h*kg)) | $V_{ss}$ (ml/kg) | $T_{1/2}$ (hr) |
|---|---|---|---|---|---|---|
| 1 | 31300 | 0.03 | 3668 | 6816 | 1185 | 0.4 |
| 2 | 26000 | 0.03 | 2861 | 8738 | 576 | 7.6 |
| 3 | 25600 | 0.03 | 3918 | 6381 | 653 | 0.03 |
| Avg. | 27633 | 0.03 | 3482 | 7312 | 804 | 2.67 |
| SD | 1837 | — | 319 | 724 | 191 | 2.45 |

Figure 17:
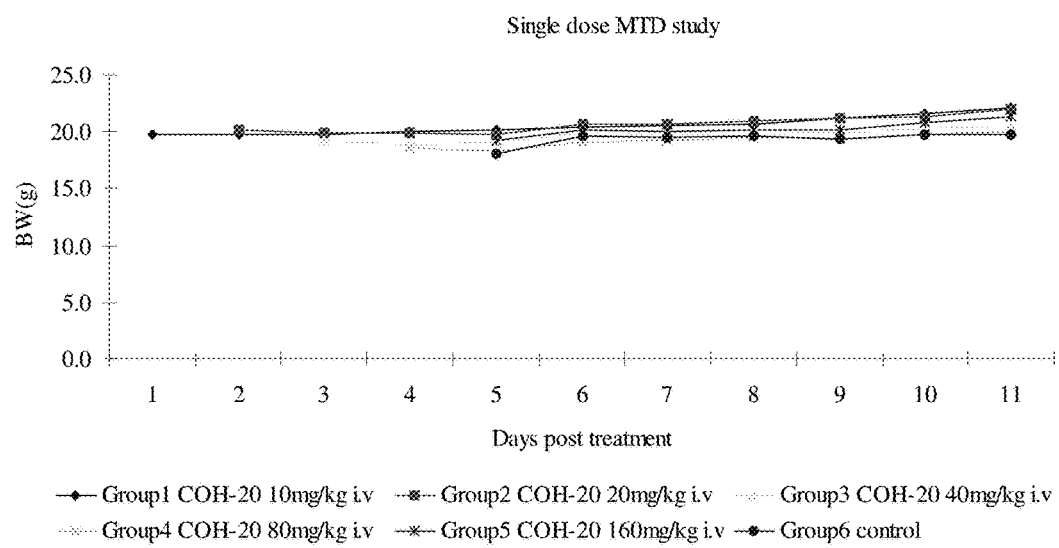
FIG. 17: COH20 maximal tolerated dose determination in normal mice.

In order to determine the maximal tolerated dose of COH20, COH20 was administered to mice intravenously at dosages ranging from 10 to 160 mg/kg. Other than one mouse that died in the 160 mg/kg group, body weight remained stable for all treatment groups, indicating that COH20 is a tolerable compound with minimal toxicity (FIG. 17). There was no evidence of lethal iron chelation or induction of methemoglobulin, further indicating that COH20 has no significant iron chelation side effects.

Figure 18:
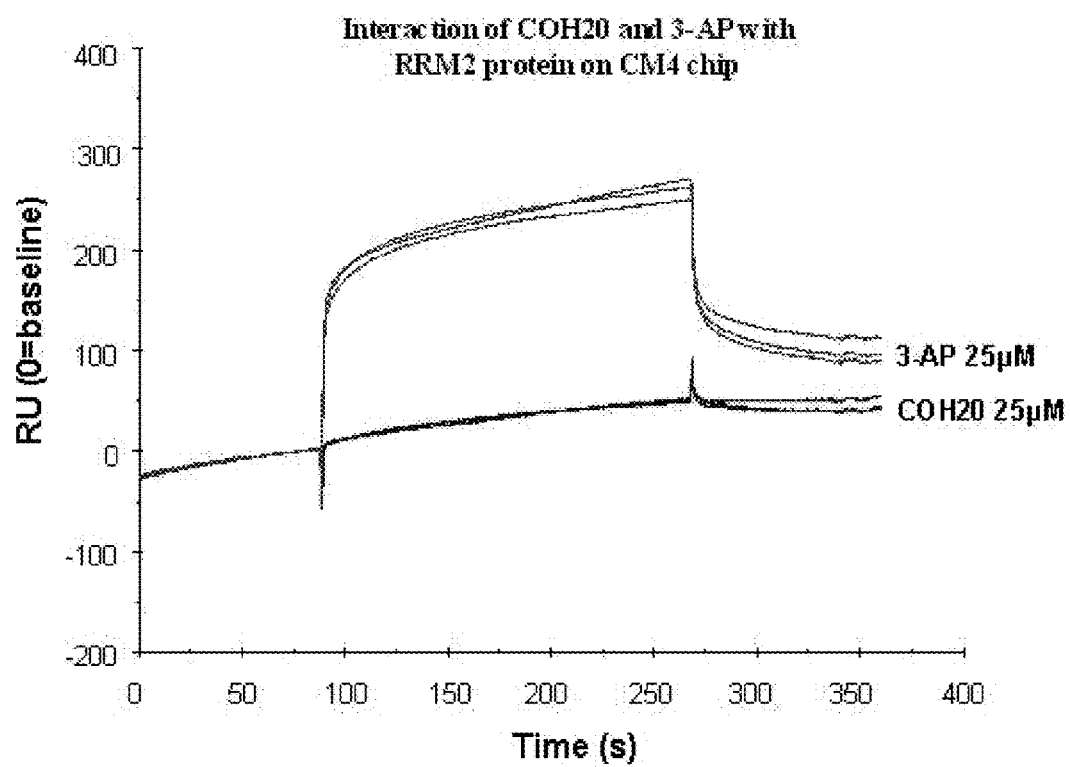
FIG. 18: Biacore analysis of RRM2 binding to COH20 and 3-AP.

A Biacore T100 instrument was used to study the ligand-protein interaction between COH20 or 3-AP and RRM2. Wild-type RRM2 was isolated and immobilized onto CM4 sensor chips using standard amine-coupling methods at 25° C. and a flow rate of 10 μL/minute. Specifically, the carboxymethyl dextran surfaces of the flow cells were activated with a 7-min injection of a 1:1 ratio of 0.4 M (N-ethyl-NO-(3-dimethylaminopropyl) carbodiimide (EDC) and 0.1 M N-hydroxysuccinimide (NHS). RRM2 was diluted in 10 mM sodium acetate, pH 4.5, to 25 μg/ml and injected over target flow cell for target immobilization 8000RU. 10 mM sodium acetate, pH 4.5 buffer was injected into the reference flow cell for blank immobilization. The remaining activated surface was blocked with a 7-min injection of 1M ethanolamine-HCl, pH 8.5. Phosphate-buffered saline (PBS) was used as a running buffer during immobilization. COH20 and 3-AP were dissolved in DMSO to prepare 100 mM stock solutions. The compounds were then diluted serially in running buffer (PBS, 1.5% DMSO, 10-fold carboxymethyl dextran, 0.002% Methyl-6-O—(N-heptylcarbamoyl)-α-D-glucoyranoside) to the appropriate running concentrations. Samples were injected over the reference flow cell and target flow cell (with immobilized RRM2) at a flow rate of 60 μL/min at 25° C. Association and dissociation were measured for 180 seconds and 60 seconds, respectively. All compounds were tested in triplicate at five different concentrations. Concentration series for each compound were done at least twice. Within a given compound concentration series, the samples were randomized to minimize systematic errors. Between samples, the sensor chip was regenerated by injection of 0.3% SDS for 30 seconds. The results showed a significant interaction between COH20 and RRM2, but not between COH20 and 3-AP (FIG. 18).

Figure 19:
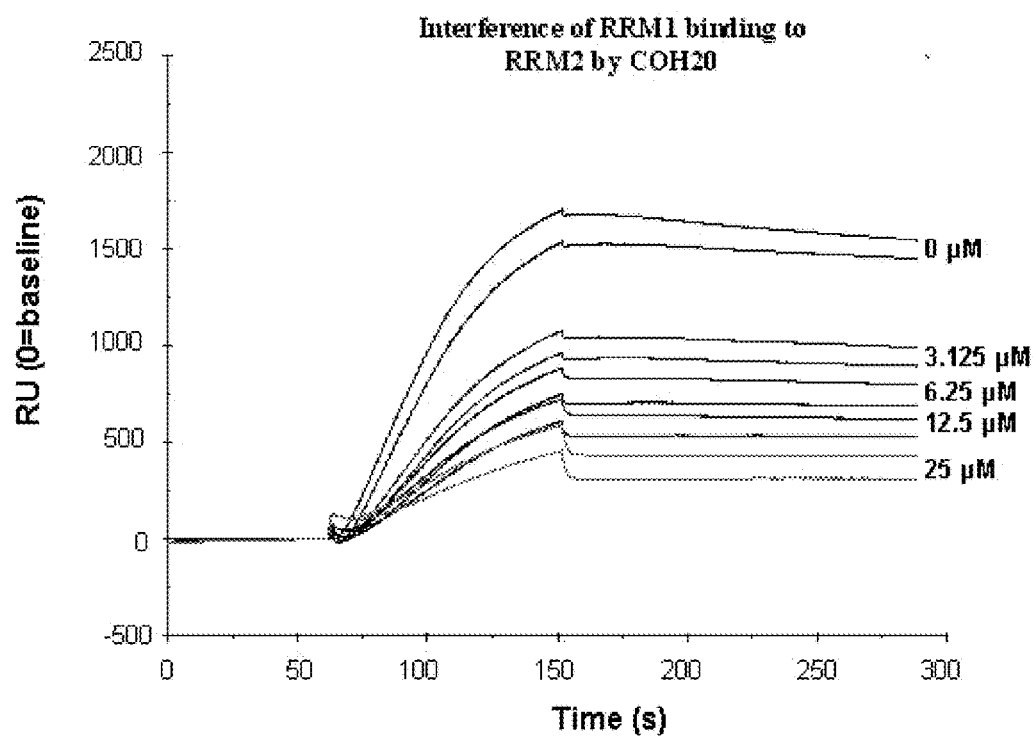
FIG. 19: Interference of RRM1 binding to RRM2 by COH20.
Figure 20:
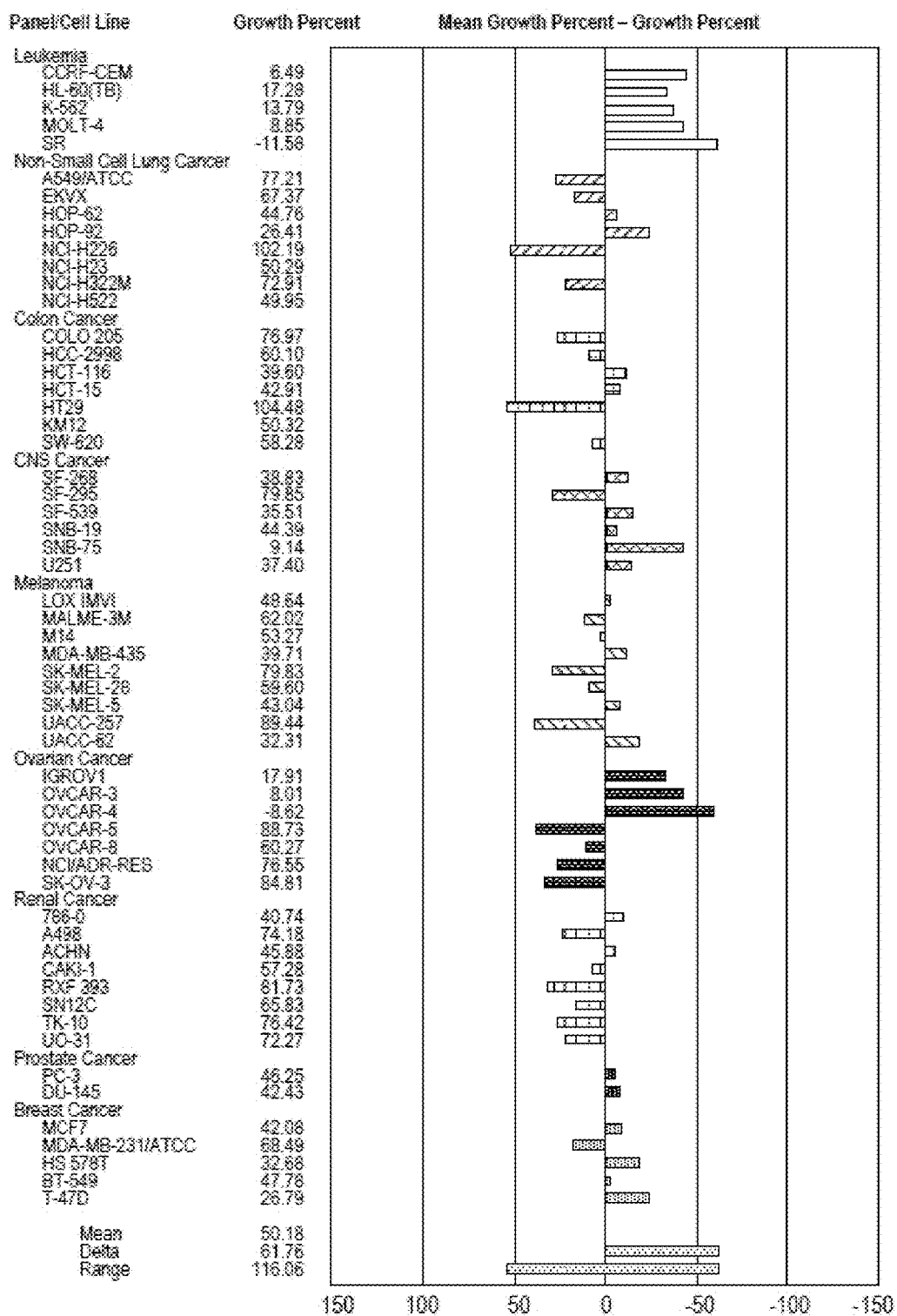
FIG. 20: Inhibition of cancer cell growth by single-dose administration of COH29.
Figure 21:
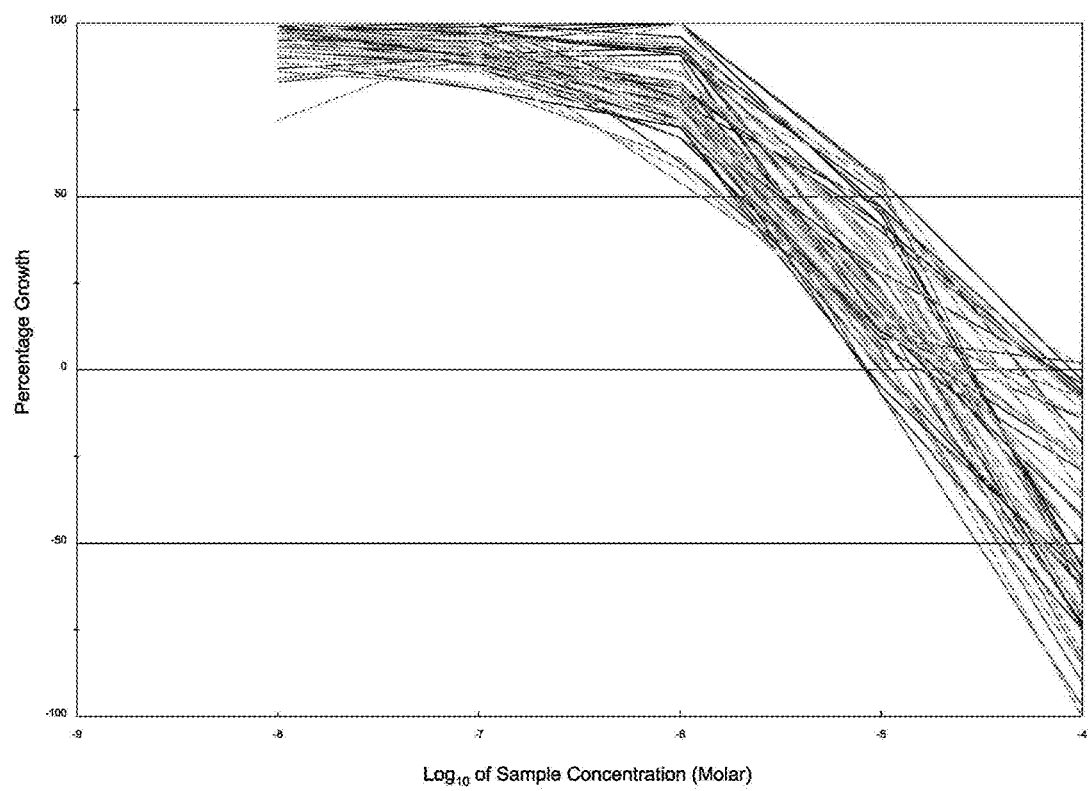
FIG. 21: Inhibition of cancer cell growth by multiple-dose administration of COH29.
Figure 22A:
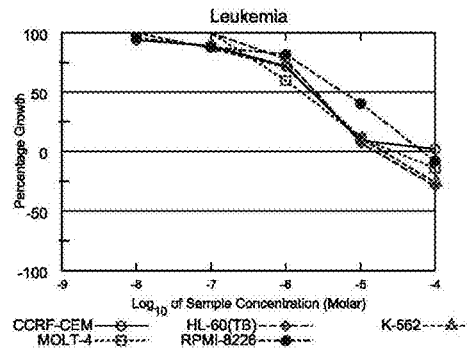
FIGS. 22A-22I: Inhibition of cancer cell growth by multiple-dose administration of COH29. Results are grouped by cell line tissue of origin. Cell line legend for FIGS. 22A-22I: leukemia, non-small cell lung cancer, colon cancer, CNS cancer, melanoma, ovarian cancer, renal cancer, prostate cancer, breast cancer, respectively.
Figure 22B:
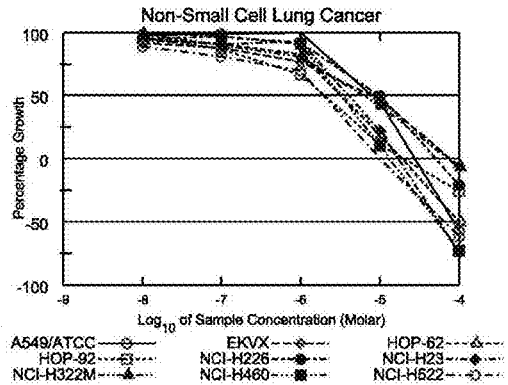
Figure 22C:
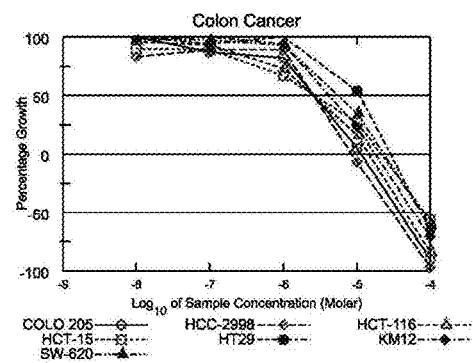
Figure 22D:
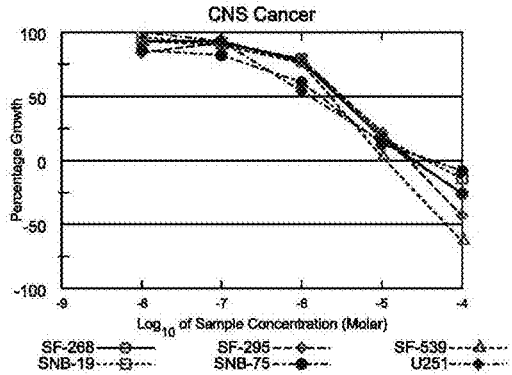
Figure 22E:
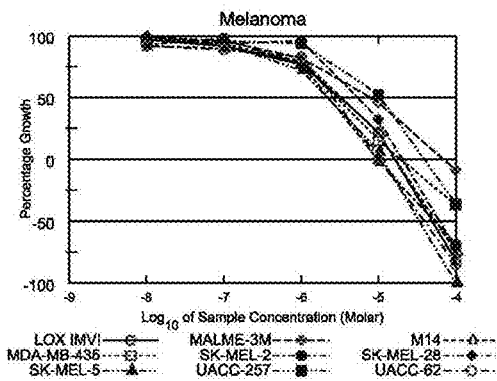
Figure 22F:
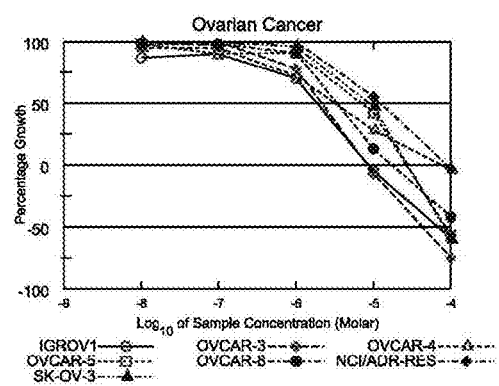
Figure 22G:
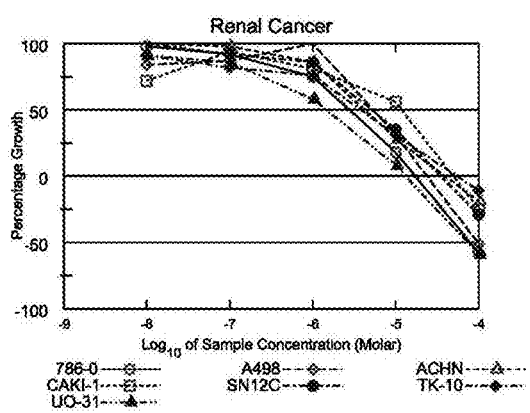
Figure 22H:
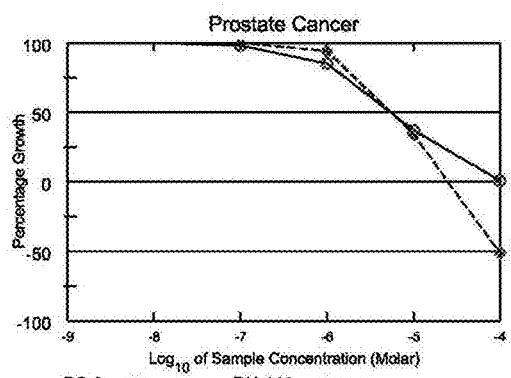
Figure 22I:
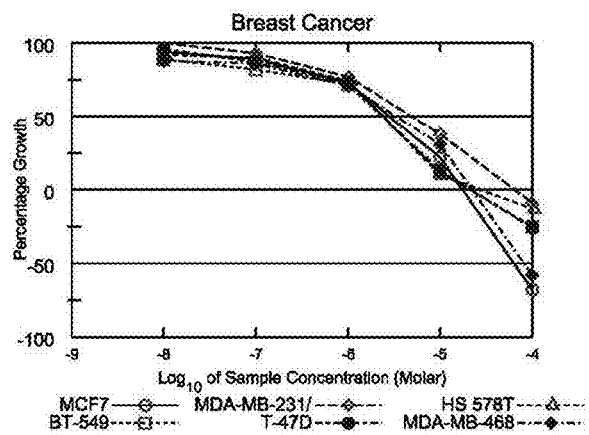
Figure 24:
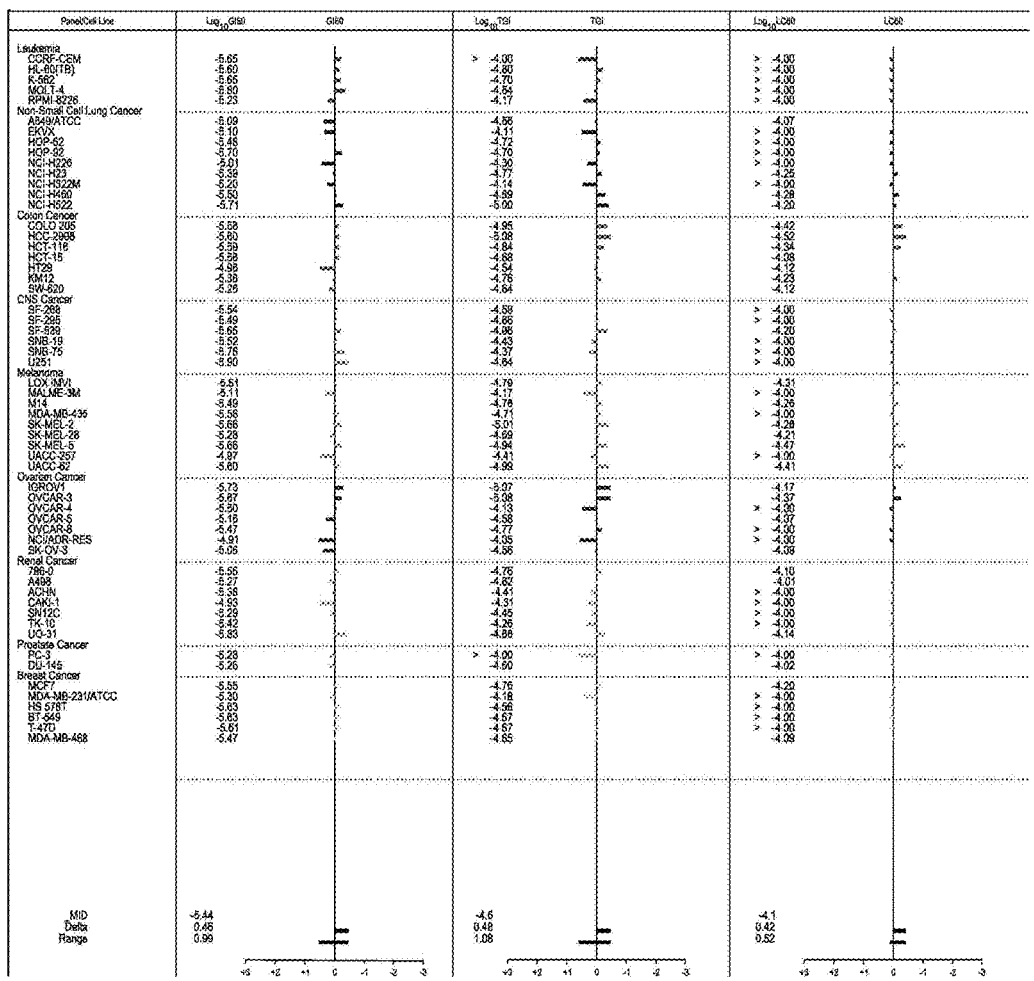
FIG. 24: Inhibition of cancer cell growth by multiple dose administration of COH29.

The Biacore T100 was also used to analyze the ability of COH20 to interfere with binding of RRM2 to RRM1. Fixed concentrations of RRM1 (1 μM) in the absence and presence of a two-fold dilution concentration series of COH20 (3.125-25 μM) were injected over a reference flow cell and a target flow cell (with immobilized RRM2) at a flow rate 30 μL/min at 25° C. Association and dissociation were measured for 90 seconds and 60 seconds, respectively. Duplicates runs were performed using the same conditions. Between samples, the sensor chip was regenerated by injection of 0.3% SDS, 0.2 M $Na_2CO_3$ for 30 seconds. COH20 was found to interrupt the RRM1/RRM2 interaction at the interface (FIG. 19).

The cytotoxic efficacy of COH20 will be tested in vivo using a mouse xenograft model. Xenograft tumor models will be created using human cancer cell lines such as KB, KBHURs, and KBGem. For establishment of the KB xenograft model, 1-5 $10^6$ KB cells in a volume of 0.1 ml saline will be injected into the right hind flank of 5-6 week old nude female mice. Tumor volume will be monitored twice weekly using digital calipers. When tumor volume reaches approximately 100-160 $mm^3$, mice will be divided into groups of ten such that the median and mean body weight and tumor volume are roughly the same for all mice within a group. COH20 will be administered either 1) alone in a single dose to determine effective dosage, 2) alone at various intervals for a scheduling study, or 3) in combination with known cancer therapeutics such as chemotherapeutics. During a monitoring period of approximately four weeks, changes in tumor cell growth, body weight, organ dysfunction, and iron chelating side effects will be analyzed at various timepoints. Following the monitoring period, mice will be euthanized and tissue, tumor, and plasma will be analyzed by visual and histological examination. Based on the cytotoxicity of COH20 towards various cancer cell lines in vitro, it is expected that mice treated with COH20 will exhibit higher survival rates, decreased tumor growth, and fewer tumor-related side effects (e.g., weight loss, organ dysfunction).

The structure of NCI-3 analogs such as COH20 and COH29 may be refined and optimized by generating various analogs and analyzing their binding to RRM2 and the RRM1/RRM2 complex using site-directed mutagenesis studies, Biacore analysis, and NMR STD experiments. X-ray crystallography studies may be performed to determine the three-dimensional structure of the COH20-RRM2 complex. Using these tools, additional RR inhibitors may be generated with higher potency, greater selectivity, and lower toxicity.

As shown above, the RRM2 mutant G233V enhanced COH20 inhibitor activity. Additional hydrophobic interactions between the valine side chain and the bound ligand are believed to contribute to enhanced binding and inhibition, suggesting that an additional hydrophobic side chain extending from COH20 could optimize binding affinity. Therefore, COH20 analogs that contain these hydrophobic side chains (e.g. COH1, COH2, COH4, COH29, compounds having Structure I, and compounds selected from Group I) are also likely to be RR inhibitors.

Example 4: Synthesis and Purification of COH29

COH29 was synthesized using the synthesis pathway outlined in FIG. 26.

Step 1: Conversion of 1,2-dimethoxybenzene (veratrole) to 1-(3,4-dimethoxyphenyl)-2-phenylethanone (Intermediate 1)

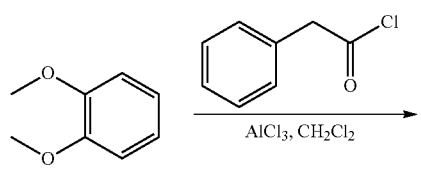

-continued

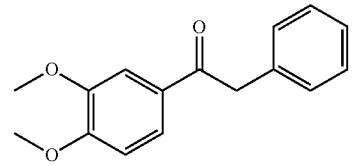

Intermediate 1 was synthesized in a reaction vessel equipped with a bubbler vented to a cold finger trap. Phenylacetyl chloride (151 mL, 1.12 mol) was added drop-wise over 30 minutes to a stirring suspension of anhydrous $AlCl_3$ (161 g, 1.21 mol) in dichloromethane (DCM; $CH_2Cl_2$, 600 mL) at 0° C. under nitrogen. Veratrole (129 mL, 1.00 mol) was added drop-wise over six hours, maintaining the internal temperature below 10° C. Upon completion of addition, the cooling bath was removed. After 16 hours at ambient temperature, the reaction was cooled to 0° C. and quenched by drop-wise addition of 2N HCl (700 mL) while maintaining the internal temperature below 20° C. The organic layer was washed with water (600 mL) and saturated aqueous $NaHCO_3$ (500 mL), filtered through CELITE®, and concentrated under reduced pressure to approximately 400 mL total volume. Hexanes (1.7 L) were added and the product precipitated with vigorous stirring. The resulting solid was filtered and the filter cake was washed with hexanes (2×250 mL). The solid was dried in vacuo at 50° C. to afford 1-(3,4-dimethoxyphenyl)-2-phenylethanone (Intermediate 1; 213 g, 831 mmol, 83% yield) as an off-white solid.

Step 2: Conversion of Intermediate 1 to 4-(3,4-dimethoxyphenyl)-5-phenylthiazol-2-amine (Intermediate 2)

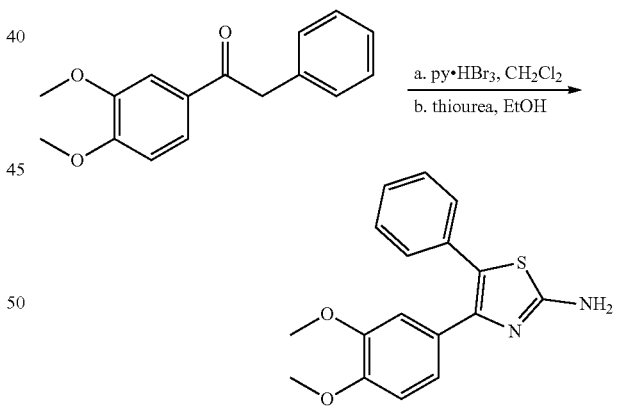

Intermediate 2 was synthesized in a reaction vessel equipped with a bubbler vented to a cold finger trap. Intermediate 1 (213 g, 831 mmol) and pyridinium tribromide (315 g, 886 mmol) were dissolved in DCM (1.2 L) under nitrogen. After five hours at ambient temperature, the reaction mixture was cooled in an ice batch and quenched with water (750 mL) while maintaining the internal temperature below 20° C. The organic layer was washed with water (750 mL) and concentrated to dryness. The resulting slurry was taken up in ethanol (1.2 L) and cooled to 20° C., and thiourea (114 g, 1.48 mol) was added. Upon addition completion, the reaction was stirred at ambient temperature for 24 hours. The reaction was concentrated under reduced pressure and the resulting slurry was partitioned between EtOAc (1.0 L) and 2N NaOH (800 mL). The emulsion was allowed to separate, and the aqueous layer was extracted with EtOAc (750 mL). The combined organic layers were washed with water (250 mL) and concentrated under reduced pressure. The resulting solid was triturated with Et$_2$O (1.5 L) and filtered, and the filter cake was washed with Et$_2$O (200 mL). The product was dried in vacuo at 50° C. to afford 4-(3,4-dimethoxyphenyl)-5-phenylthiazol-2-amine (Intermediate 2; 230 g, 736 mmol, 89% yield for 2 steps) as a tan solid.

Step 3: Conversion of Intermediate 2 to N-(4-(3,4-dimethoxyphenyl)-5-phenylthiazol-2-yl)-3,4-dimethoxybenzamide (Intermediate 3)

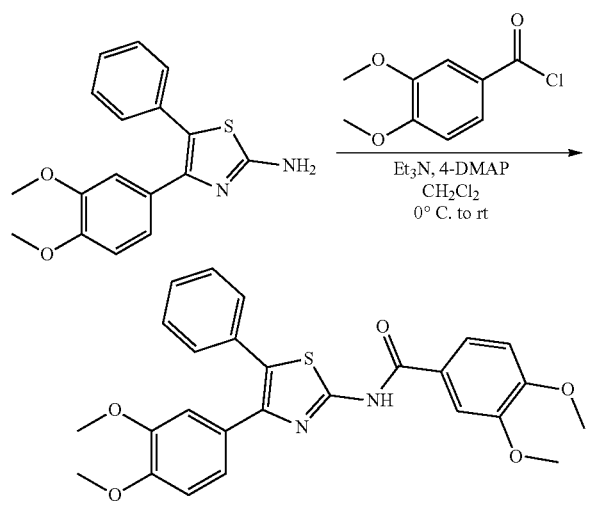

Intermediate 3 was synthesized in a reaction vessel equipped with a bubbler vented to a cold finger trap. Thionyl chloride (100 mL, 1.36 mol) was added drop-wise over two hours to a cooled solution of 3,4-dimethoxybenzoic acid (250 g, 1.36 mol) in dimethylformamide (DMF; 20 mL) in CH$_2$Cl$_2$ (1.0 L) while maintaining an internal temperature below 15° C. After addition completion, the reaction was stirred for three hours at ambient temperature, then concentrated to dryness under reduced pressure. Acid chloride (164 g, 818 mmol, 1.5 eq) was added portion-wise to a stirring suspension of Intermediate 2 (170 g, 545 mmol), 4-dimethylamino pyridine (4-DMAP; 6.73 g, 54.5 mmol, 10 mol %), and Et$_3$N (384 mL, 2.73 mol) in DMF (1.0 L) under nitrogen, maintaining an internal temperature below 20° C. The reaction was stirred for 15 hours at ambient temperature, then the remaining acid chloride (112 g, 545 mmol) was portion-wise. After six hours at ambient temperature, the reaction mixture was quenched with saturated aqueous sodium NaHCO$_3$ (500 mL), washed with water (500 mL), and concentrated under reduced pressure. The product was purified by flash chromatography (0-5% MeOH/CH$_2$Cl$_2$. The combined chromatographic fractions were concentrated to dryness under reduced pressure. The solid was dried in vacuo at 50° C. to afford N-(4-(3,4-dimethoxyphenyl)-5-phenylthiazol-2-yl)-3,4-dimethoxybenzamide (Intermediate 3; 245 g, 515 mmol, 70%) as an off-white solid.

Step 4: Conversion of Intermediate 3 to COH29

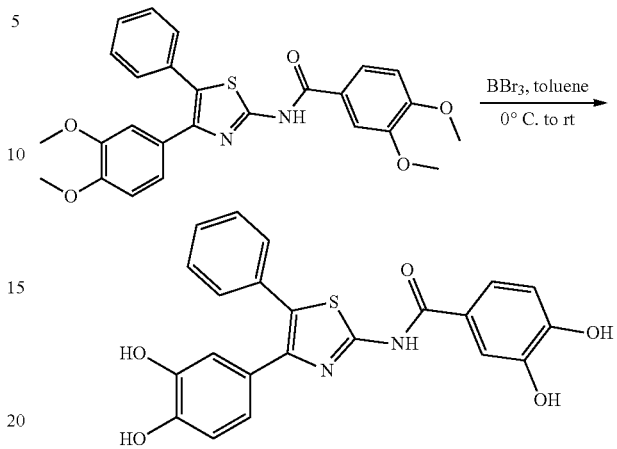

COH29 was synthesized in a reaction vessel equipped with a bubbler vented to a cold finger trap. Boron tribromide (BBr$_3$; 191 mL, 1.98 mol) was slowly added to a stirring solution of Intermediate 3 (245 g, 515 mmol) in toluene (1.2 L) under nitrogen, maintaining the internal temperature below 15° C. Upon addition completion, the reaction was allowed to warm to ambient temperature and stirred for five hours. The reaction mixture was cooled and slowly quenched with EtOH (800 mL) while maintaining the internal temperature below 20° C. Upon addition completion, the solution was stirred for two hours at ambient temperature and concentrated under reduced pressure. The resulting solid was triturated with DCM (1.0 L) and filtered, and the filter cake was washed with DCM (100 mL). The resulting solid was taken up in hot EtOH (400 mL) and slowly added to water (2.4 L) to induce precipitation. The resulting slurry was stirred for two hours at ambient temperature and filtered, and the filter cake was washed with water (200 mL). This trituration process was repeated three additional times to afford an off-white solid. The resulting solid was dried at 50° C. under vacuum for 24 hours, then at 125° C. under vacuum for 24 hours to afford COH29 (118 g, 281 mmol, 55%)

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Angus, S. P., et al. 2002. J Biol Chem 277:44376-44384.
2. Berge et al. 1977. J Pharm Sci 66:1-19.
3. Chabes, A. L., et al. 2004. J Biol Chem 279:10796-10807.
4. Chang, C. H, Cheng, Y. C. 1979. Cancer Res 39:5081-5086.
5. Chen, S-Y., et al. 2000. Antisense Nucleic Acid Drug Dev 10:111-116.
6. Cooperman, B. S., Kashlan, O. B. 2003. Adv Enzyme Regul 43:167-182.

7. Cory, J. G., Sato, A. 1983. Mol Cell Biochem 53-54:257-66.
8. Currie, R. A. 1998. J Biol Chem 273:1430-1434.
9. Elledge, S. J., Davis, R. W. 1990. Genes Dev 4:740-751.
10. Fan, H., et al. 1997. Proc Natl Acad Sci USA 94:13181-13186.
11. Fan, H., et al. 1998. Cancer Res 58:1650-1653.
12. Filatov, D., Thelander, L. 1995. J Biol Chem 270:25239-25243.
13. Goan, Y. G., et al. 1999. Cancer Res 59:4204-4207.
14. Guittet, O., et al. 2001. J Biol Chem 276:40647-40651.
15. Huang, A., et al. 1997. Cancer Res 57:4876-4881.
16. Jordan, A., Reichard, P. 1998. Annu Rev Biochem 67:71-98.
17. Kimura, T., et al. 2003. Nature Genetics 34:440-445.
18. Kuschak, T. I., et al. 2002. Gene (Amst.) 238:351-365.
19. Lassmann, G., et al. 1992. Biochem Biophys Res Commun 188:879-887.
20. Le, N. T., Richardson, D. R. 2002. Biochim Biophys Acta 1603:31-46.
21. Liu, X., et al. 2004. Biochem Pharmacol 67:1499-1511.
22. Liu, X., et al. 2005. Biochem Pharmacol 70:1288-1297.
23. Liu, X., et al. 2006. Clin Cancer Res 12:6337-6344.
24. Lozano, G., Elledge, S. J. 2000. Nature 404:24-25.
25. Nakano, K. et al. 2000. Oncogene 19:4283-4289.
26. Nocentini, G. 1996. Crit Rev Oncol Hematol 22:89-126.
27. Nyholm, S., et al. 1993. Biochemistry 32:11569-11574.
28. Ochiai, E., et al. 1990. J Biol Chem 265:15758-15761.
29. Remington, 2000, The Science and Practice of Pharmacy (Gennaro ed. 20th edition, Williams & Wilkins PA, USA).
30. Shao, J., et al. 2005. Biochem Pharmacol 69:627-634.
31. Tanaka, H., et al. 2000. Nature 404:42-49.
32. Thelander, L., Berg, P. 1998. Mol Cell Biol 6:3433-3442.
33. Wright, J. A., et al. 1990. Biochem Cell Biol 68:1364-1371.
34. Xue, L., et al. 2007. Cancer Res 63:980-986.
35. Yamaguchi, T., et al. 2001. Cancer Res 61:8256-8262.
36. Yen, Y., et al. 1994. Cancer Res 54:3686-3691.
37. Zhou, B. S., et al. 1995. Cancer Res 55:1328-1333.
38. Zhou, B. S., et al. 1998. Clin Exp Metastasis 16:43-49.
39. Zhou, B., et al. 2003. Cancer Res 63:6583-6594.

What is claimed is:

1. A compound having the formula

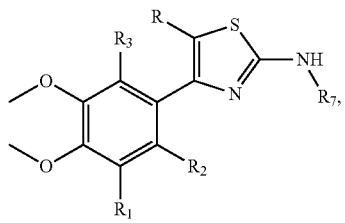

Structure V wherein,
R is substituted or unsubstituted aryl,
$R_1$, $R_2$, $R_3$, and $R_7$ are independently hydrogen, —OH, —NH$_2$, —SH, —CN, —CF$_3$, —NO$_2$, oxo, halogen, $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl,
$R_{17}$ is —OH, —NH$_2$, —SH, —CN, —CF$_3$, —NO$_2$, oxo, halogen, $R_{20}$-substituted or unsubstituted alkyl, $R_{20}$-substituted or unsubstituted heteroalkyl, $R_{20}$-substituted or unsubstituted cycloalkyl, $R_{20}$-substituted or unsubstituted heterocycloalkyl, $R_{20}$-substituted or unsubstituted aryl, or $R_{20}$-substituted or unsubstituted heteroaryl,
$R_{20}$ is —OH, —NH$_2$, —SH, —CN, —CF$_3$, —NO$_2$, oxo, halogen, $R_{21}$-substituted or unsubstituted alkyl, $R_{21}$-substituted or unsubstituted heteroalkyl, $R_{21}$-substituted or unsubstituted cycloalkyl, $R_{21}$-substituted or unsubstituted heterocycloalkyl, $R_{21}$-substituted or unsubstituted aryl, or $R_{21}$-substituted or unsubstituted heteroaryl, and
$R_{21}$ is —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, or unsubstituted heteroaryl.

2. The compound of claim 1, wherein
R is substituted aryl.

3. The compound of claim 1, wherein
$R_1$, $R_2$, $R_3$, and $R_7$ are independently hydrogen, —OH, —NH$_2$, —SH, —CN, —CF$_3$, —NO$_2$, oxo, or halogen.

4. The compound of claim 1, wherein
$R_1$, $R_2$, $R_3$, and $R_7$ are independently hydrogen.

5. The compound of claim 1, wherein
$R_1$, $R_2$, $R_3$, and $R_7$ are independently $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl.

6. The compound of claim 1, wherein
$R_1$, $R_2$, $R_3$, and $R_7$ are independently $R_{17}$-substituted or unsubstituted alkyl, $R_{17}$-substituted or unsubstituted heteroalkyl.

7. A method of synthesizing a compound having the formula:

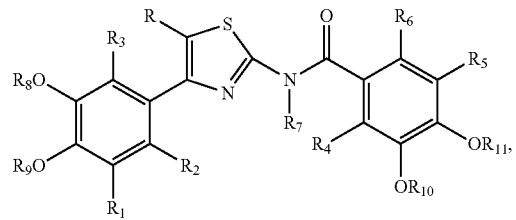

Structure VIA wherein said method comprising contacting a compound having the formula

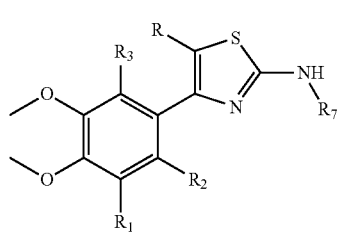

Structure V with a compound having the formula

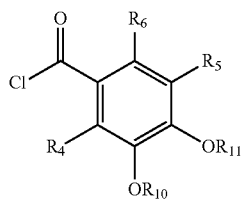

wherein,

R is substituted or unsubstituted aryl, $R_1$, $R_2$, $R_3$, $R_4$, $R_5$, $R_6$ and $R_7$ are independently hydrogen, —OH, —$NH_2$, —SH, —CN, —$CF_3$, —$NO_2$, oxo, halogen, $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl, $R_8$, $R_9$, $R_{10}$ and $R_{11}$ are independently a hydroxyl protecting group, wherein $R_8$ and $R_9$ are optionally joined together to form a substituted or unsubstituted heterocycloalkyl and $R_{10}$ and $R_{11}$ are optionally joined together to form a substituted or unsubstituted heterocycloalkyl, $R_{17}$ is —OH, —$NH_2$, —SH, —CN, —$CF_3$, —$NO_2$, oxo, halogen, $R_{20}$-substituted or unsubstituted alkyl, $R_{20}$-substituted or unsubstituted heteroalkyl, $R_{20}$-substituted or unsubstituted cycloalkyl, $R_{20}$-substituted or unsubstituted heterocycloalkyl, $R_{20}$-substituted or unsubstituted aryl, or $R_{20}$-substituted or unsubstituted heteroaryl, $R_{20}$ is —OH, —$NH_2$, —SH, —CN, —$CF_3$, —$NO_2$, oxo, halogen, $R_{21}$-substituted or unsubstituted alkyl, $R_{21}$-substituted or unsubstituted heteroalkyl, $R_{21}$-substituted or unsubstituted cycloalkyl, $R_{21}$-substituted or unsubstituted heterocycloalkyl, $R_{21}$-substituted or unsubstituted aryl, or $R_{21}$-substituted or unsubstituted heteroaryl, and $R_{21}$ is —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, or unsubstituted heteroaryl.

8. The method of claim 7, wherein R is substituted aryl.

9. The method of claim 7, wherein $R_1$, $R_2$, $R_3$, $R_4$, $R_5$, $R_6$ and $R_7$ are independently hydrogen, —OH, —$NH_2$, —SH, —CN, —$CF_3$, —$NO_2$, oxo, or halogen.

10. The method of claim 7, wherein $R_1$, $R_2$, $R_3$, $R_4$, $R_5$, $R_6$ and $R_7$ are hydrogen.

11. The method of claim 7, wherein $R_1$, $R_2$, $R_3$, $R_4$, $R_5$, $R_6$ and $R_7$ are independently $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl.

12. The method of claim 7, wherein $R_8$, $R_9$, $R_{10}$ and $R_{11}$ are independently substituted or unsubstituted alkyl, substituted or unsubstituted heteroalkyl, substituted or unsubstituted aryl, or a substituted silyl.

13. The method of claim 7, wherein $R_8$, $R_9$, $R_{10}$ and $R_{11}$ are independently an activated ethylene protecting group, a benzyl ether protecting group, or a silicon-based carbonate protecting group.

14. The method of claim 7, wherein $R_8$ and $R_9$ are optionally joined together to form an acetal protecting group and $R_{10}$ and $R_{11}$ are optionally joined together to form an acetal protecting group.

15. The method of claim 7, wherein said acetal is a diphenyl methylene acetal.

16. A method of using a first compound having the formula:

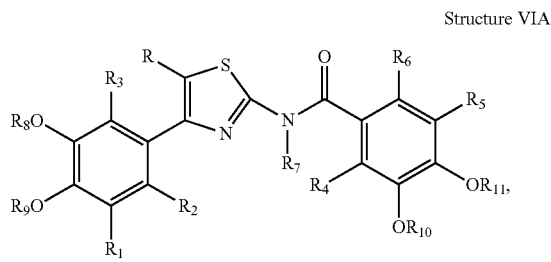

Structure VIA wherein,

R is substituted or unsubstituted aryl, $R_1$, $R_2$, $R_3$, $R_4$, $R_5$, $R_6$ and $R_7$ are independently hydrogen, —OH, —$NH_2$, —SH, —CN, —$CF_3$, —$NO_2$, oxo, halogen, $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl, $R_8$, $R_9$, $R_{10}$ and $R_{11}$ are independently a hydroxyl protecting group, wherein $R_8$ and $R_9$ are optionally joined together to form a substituted or unsubstituted heterocycloalkyl and $R_{10}$ and $R_{11}$ are optionally joined together to form a substituted or unsubstituted heterocycloalkyl, $R_{17}$ is —OH, —$NH_2$, —SH, —CN, —$CF_3$, —$NO_2$, oxo, halogen, $R_{20}$-substituted or unsubstituted alkyl, $R_{20}$-substituted or unsubstituted heteroalkyl, $R_{20}$-substituted or unsubstituted cycloalkyl, $R_{20}$-substituted or unsubstituted heterocycloalkyl, $R_{20}$-substituted or unsubstituted aryl, or $R_{20}$-substituted or unsubstituted heteroaryl, $R_{20}$ is —OH, —$NH_2$, —SH, —CN, —$CF_3$, —$NO_2$, oxo, halogen, $R_{21}$-substituted or unsubstituted alkyl, $R_{21}$-substituted or unsubstituted heteroalkyl, $R_{21}$-substituted or unsubstituted cycloalkyl, $R_{21}$-substituted or unsubstituted heterocycloalkyl, $R_{21}$-substituted or unsubstituted aryl, or $R_{21}$-substituted or unsubstituted heteroaryl, and $R_{21}$ is —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, or unsubstituted heteroaryl, in the preparation of one or more additional compounds in one or more additional steps.

17. The method of claim 16, further comprising the formation of a pharmaceutical product.

18. A method of using a first compound having the formula:

Structure V

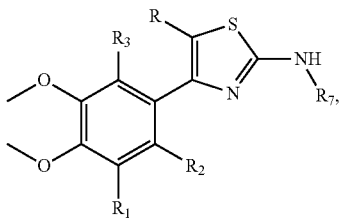

wherein,

R is substituted or unsubstituted aryl, $R_1$, $R_2$, $R_3$, and $R_7$ are independently hydrogen, —OH, —$NH_2$, —SH, —CN, —$CF_3$, —$NO_2$, oxo, halogen, $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl, $R_{17}$ is —OH, —$NH_2$, —SH, —CN, —$CF_3$, —$NO_2$, oxo, halogen, $R_{20}$-substituted or unsubstituted alkyl, $R_{20}$-substituted or unsubstituted heteroalkyl, $R_{20}$-substituted or unsubstituted cycloalkyl, $R_{20}$-substituted or unsubstituted heterocycloalkyl, $R_{20}$-substituted or unsubstituted aryl, or $R_{20}$-substituted or unsubstituted heteroaryl, $R_{20}$ is —OH, —$NH_2$, —SH, —CN, —$CF_3$, —$NO_2$, oxo, halogen, $R_{21}$-substituted or unsubstituted alkyl, $R_{21}$-substituted or unsubstituted heteroalkyl, $R_{21}$-substituted or unsubstituted cycloalkyl, $R_{21}$-substituted or unsubstituted heterocycloalkyl, $R_{21}$-substituted or unsubstituted aryl, or $R_{21}$-substituted or unsubstituted heteroaryl, and $R_{21}$ is —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, or unsubstituted heteroaryl, in preparation of a second compound.

19. The method of claim 18, wherein said second compound is a pharmaceutical product.

20. The method of claim 18, wherein said second compound is a compound having the formula:

Structure VIA

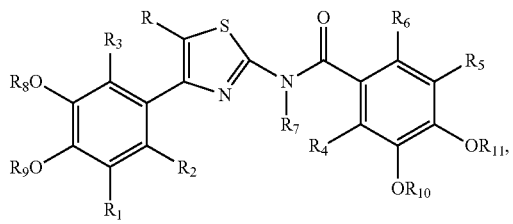

wherein $R_4$, $R_5$, and $R_6$ are independently hydrogen, —OH, —$NH_2$, —SH, —CN, —$CF_3$, —$NO_2$, oxo, halogen, $R_{17}$-substituted or unsubstituted alkyl, $R_{17}$-substituted or unsubstituted heteroalkyl, $R_{17}$-substituted or unsubstituted cycloalkyl, $R_{17}$-substituted or unsubstituted heterocycloalkyl, $R_{17}$-substituted or unsubstituted aryl, or $R_{17}$-substituted or unsubstituted heteroaryl, and $R_8$, $R_9$, $R_{10}$ and $R_{11}$ are independently a hydroxyl protecting group, wherein $R_8$ and $R_9$ are optionally joined together to form a substituted or unsubstituted heterocycloalkyl and $R_{10}$ and $R_{11}$ are optionally joined together to form a substituted or unsubstituted heterocycloalkyl.

* * * * *